US005801146A

United States Patent [19]
Davidson

[11] Patent Number: 5,801,146
[45] Date of Patent: Sep. 1, 1998

[54] COMPOUND AND METHOD FOR INHIBITING ANGIOGENESIS

[75] Inventor: Donald J. Davidson, Gurnee, Ill.

[73] Assignee: Abbott Laboratories, Abbott Park, Ill.

[21] Appl. No.: 643,219

[22] Filed: May 3, 1996

[51] Int. Cl.$^6$ .......................... A61K 38/00; A61K 35/14
[52] U.S. Cl. ........................ 514/12; 530/380; 530/324; 530/300
[58] Field of Search ..................... 514/12; 530/300, 530/324, 380

[56] References Cited

U.S. PATENT DOCUMENTS 5,639,725  6/1997  O'Reilley et al. ........................ 514/12

FOREIGN PATENT DOCUMENTS

| 9204450 | 3/1992 | WIPO . |
| 9529242 | 11/1995 | WIPO . |
| 9723500 | 7/1997 | WIPO . |

OTHER PUBLICATIONS

Scrip 2120:21 (Apr. 16, 1996).
Fidler, LJ., et al., "The Implications of Angiogenesis for the Biology and Therapy of Cancer Metastasis", *Cell,* 79:185–188 (1994).
Folkman, J., "Clinical Applications of Research on Angiongenesis", *The New England Journal of Medicine,* 333(26):1757–1763 (1995).
Folkman, J., et al., "Angiogenesis", *Journ. of Biological Chemistry,* 267(16):10931–10934 (1992).
Folkman, J., et al., "Angiogenic Factors", *Science,* 235:442–447 (1987).
Gasparini, G., et al., "Clinical Importance of the Determination of Tumor Angiogenesis in Breast Carcinoma: Much More Than a New Prognostic Tool", *Journ. of Clinical Oncology,* 13(3):765–782 (1995).
Sottrup–Jensen, L., et al., "The Primary Structure of Human Plasminogen: Isolation of Two Lysine–Binding Fragments and One Mini–Plasminogen (MW, 38,000) by Elastase––Catalyzed–Specific Limited Proteolysis", *Progress in Chemical Fibrinolysis and Thrombolysis,* 3:191–209 (1978).
Kolberg, R., "Angogenic Inhibitor Loss May Be Key To Post–Surgery Metastasis", *Journal of NIH Research,* 8:31–33 (1994).
Menhart, N., et al., "Functional Independence of the Kringle 4 and Kringle 5 Regions of Human Plasminogen", *Biochemistry,* 32:8799–8806 (1993).
Novokhatny, V. V., et al., "Domains in Human Plasminogen", *J, Mol. Biol.,* 179:215–232 (1984).

O'Reilly, M. S., et al., "Angiostatin: A Novel Angiogenesis Inhibitor That Mediates the Suppression of Metastases by a Lewis Lung Carcinoma", *Cell,* 79:315–328 (1994).
Teicher, B. A., et al., "Antiangiogenic Agents Can Increase Tumor Oxygenation and Response to Radiation Therapy", *Radiation Oncology Investigations,* 2:269–276 (1995).
Teicher, B. A., et al., "Antiangiogenic Agents Potentiate Cytotoxic Cancer Therapies against Primary and Metastatic Disease", *Cancer Research,* 52:6702–6704 (1992).
Teicher, B. A., et al., "Antiangiogenic Treatment (TNP–470/Minocycline) Increase Tissue Levels of Anticancer Drugs in Mice Bearing Lewis Lung Carcinoma", *Oncology Research,* 7(5):237–243 (1995).
Teicher, B. A., et al., "β–Cyclodextrin tetradecasulfate/ tetrahydrocortisol ± minocycline as modulators of cancer therapies in vitro and in vivo against primary and metastatic lewis lung carcinoma", *Cancer Chemother Pharmacol,* 33:229–239 (1993).
Teicher, B. A., et al., "Influence of an Anti–Angiogenic Treatment on 9L Gliosarcoma: Oxygenation and Response ot Cytotoxic Therapy", *Int. J. Cancer,* 61:732–737 (1995).
Teicher, B. A., et al., "Potentiation of Cytotoxic Cancer Therapies by TNP–470 Alone and With Other Anti–Angiogenic Agents", *Int. J. Cancer,* 57:920–925 (1994).
Teicher, B. A., et al., "Potentiation of cytotoxic therapies by TNP–470 and minocycline in mice bearing EMT–6 mammary carcinoma ", *Breast Cancer Research and Treatment,* 36:227–236 (1995).
Thewest, T., et al., "Ligand Interactions with the Kringle 5 Domain of Plasminogen", *Journal of Biological Chemistry,* 265(7):3906–3915 (1990).
Weidner, N., et al., "Tumor Angiogensis and Metastasis—Correlation in Invasive Breast Carcinoma", *The New England Journal of Medicine,* 324(1):1–8 (1991).
Thewes et al. (Apr. 8, 1987) Isolation, purification and 1H–NMR characterization of a kringle 5 domain fragment from human plasminogen. Biochimica et Biophysica Acta 912(2): 254–269.
Varadi et al. (Nov. 16, 1981) Kringle 5 of human plasminogen carries a benzamidine–binding site. Biochem. Biophys. Res. Commun. 103(1): 97–102.
McCance et al. (Dec. 23, 1994) Amino acid residues of the kringle–4 and kringle–5 domains of human plasminogen that stabilize their interactions with w–amino acid ligands. J. Biol. Chem 269(51): 32405–32410.

*Primary Examiner*—Robert A. Wax
*Assistant Examiner*—Einar Stole
*Attorney, Agent, or Firm*—Gregory W. Steele; Dianne Casuto

[57] ABSTRACT

Mammalian kringle 5 is disclosed as a compound for treating angiogenic diseases. Methods and compositions for inhibiting angiogenic diseases are also disclosed.

14 Claims, 12 Drawing Sheets

| | | | | | | | | | | | | | | |
|---|---|---|---|---|---|---|---|---|---|---|---|---|---|---|
| GLU 1 | PRO | LEU | ASP | ASP 5 | TYR | VAL | ASN | THR | GLN 10 | GLY | ALA | SER | LEU | PHE 15 |
| SER | VAL | THR | LYS | LYS 20 | GLN | LEU | GLY | ALA | GLY 25 | SER | ILE | GLU | GLU | CYS 30 |
| ALA | ALA | LYS | CYS | GLU 35 | GLU | ASP | GLU | GLU | PHE 40 | THR | CYS | ARG | ALA | PHE 45 |
| GLN | TYR | HIS | SER | LYS 50 | GLU | GLN | GLN | CYS | VAL 55 | ILE | MET | ALA | GLU | ASN 60 |
| ARG | LYS | SER | SER | ILE 65 | ILE | ILE | ARG | MET | ARG 70 | ASP | VAL | VAL | LEU | PHE 75 |
| GLU | LYS | LYS | VAL | TYR 80 | LEU | SER | GLU | CYS | LYS 85 | THR | GLY | ASN | GLY | LYS 90 |
| ASN | TYR | ARG | GLY | THR 95 | MET | SER | LYS | THR | LYS 100 | ASN | GLY | ILE | THR | CYS 105 |
| GLN | LYS | TRP | SER | SER 110 | THR | SER | PRO | HIS | ARG 115 | PRO | ARG | PHE | SER | PRO 120 |
| ALA | THR | HIS | PRO | SER 125 | GLU | GLY | LEU | GLU | GLU 130 | ASN | TYR | CYS | ARG | ASN 135 |
| PRO | ASP | ASN | ASP | PRO 140 | GLN | GLY | PRO | TRP | CYS 145 | TYR | THR | THR | ASP | PRO 150 |
| GLU | LYS | ARG | TYR | ASP 155 | TYR | CYS | ASP | ILE | LEU 160 | GLU | CYS | GLU | GLU | GLU 165 |
| CYS | MET | HIS | CYS | SER 170 | GLY | GLU | ASN | TYR | ASP 175 | GLY | LYS | ILE | SER | LYS 180 |
| THR | MET | SER | GLY | LEU 185 | GLU | CYS | GLN | ALA | TRP 190 | ASP | SER | GLN | SER | PRO 195 |
| HIS | ALA | HIS | GLY | TYR 200 | ILE | PRO | SER | LYS | PHE 205 | PRO | ASN | LYS | ASN | LEU 210 |
| LYS | LYS | ASN | TYR | CYS 215 | ARG | ASN | PRO | ASP | ARG 220 | GLU | LEU | ARG | PRO | TRP 225 |
| CYS | PHE | THR | THR | ASP 230 | PRO | ASN | LYS | ARG | TRP 235 | GLU | LEU | CYS | ASP | ILE 240 |
| PRO | ARG | CYS | THR | THR 245 | PRO | PRO | PRO | SER | SER 250 | GLY | PRO | THR | TYR | GLN 255 |
| CYS | LEU | LYS | GLY | THR 260 | GLY | GLU | ASN | TYR | ARG 265 | GLY | ASN | VAL | ALA | VAL 270 |

(SEQ ID NO:1)

FIG.1a

```
THR VAL SER GLY HIS THR CYS GLN HIS TRP SER ALA GLN THR PRO
              275              280              285
HIS THR HIS ASN ARG THR PRO GLU ASN PHE PRO CYS LYS ASN LEU
              290              295              300
ASP GLU ASN TYR CYS ARG ASN PRO ASP GLY LYS ARG ALA PRO TRP
              305              310              315
CYS HIS THR THR ASN SER GLN VAL ARG TRP GLU TYR CYS LYS ILE
              320              325              330
PRO SER CYS ASP SER SER PRO VAL SER THR GLU GLN LEU ALA PRO
              335              340              345
THR ALA PRO PRO GLU LEU THR PRO VAL VAL GLN ASP CYS TYR HIS
              350              355              360
GLY ASP GLY GLN SER TYR ARG GLY THR SER SER THR THR THR THR
              365              370              375
GLY LYS LYS CYS GLN SER TRP SER SER MET THR PRO HIS ARG HIS
              380              385              390
GLN LYS THR PRO GLU ASN TYR PRO ASN ALA GLY LEU THR MET ASN
              395              400              405
TYR CYS ARG ASN PRO ASP ALA ASP LYS GLY PRO TRP CYS PHE THR
              410              415              420
THR ASP PRO SER VAL ARG TRP GLU TYR CYS ASN LEU LYS LYS CYS
              425              430              435
SER GLY THR GLU ALA SER VAL VAL ALA PRO PRO VAL VAL LEU
              440              445              450
LEU PRO ASP VAL GLU THR PRO SER GLU GLU ASP CYS MET PHE GLY
              455              460              465
ASN GLY LYS GLY TYR ARG GLY LYS ARG ALA THR THR VAL THR GLY
              470              475              480
THR PRO CYS GLN ASP TRP ALA ALA GLN GLU PRO HIS ARG HIS SER
              485              490              495
ILE PHE THR PRO GLU THR ASN PRO ARG ALA GLY LEU GLU LYS ASN
              500              505              510
TYR CYS ARG ASN PRO ASP GLY ASP VAL GLY GLY PRO TRP CYS TYR
              515              520              525
THR THR ASN PRO ARG LYS LEU TYR ASP TYR CYS ASP VAL PRO GLN
              530              535              540
```

FIG.1b

```
CYS ALA ALA PRO SER PHE ASP CYS GLY LYS PRO GLN VAL GLU PRO
                545             550                 555
LYS LYS CYS PRO GLY ARG VAL VAL GLY GLY CYS VAL ALA HIS PRO
                560             565                 570
HIS SER TRP PRO TRP GLN VAL SER LEU ARG THR ARG PHE GLY MET
                575             580                 585
HIS PHE CYS GLY GLY THR LEU ILE SER PRO GLU TRP VAL LEU THR
                590             595                 600
ALA ALA HIS CYS LEU GLU LYS SER PRO ARG PRO SER SER TYR LYS
                605             610                 615
VAL ILE LEU GLY ALA HIS GLN GLU VAL ASN LEU GLU PRO HIS VAL
                620             625                 630
GLN GLU ILE GLU VAL SER ARG LEU PHE LEU GLU PRO THR ARG LYS
                635             640                 645
ASP ILE ALA LEU LEU LYS LEU SER SER PRO ALA VAL ILE THR ASP
                650             655                 660
LYS VAL ILE PRO ALA CYS LEU PRO SER PRO ASN TYR VAL VAL ALA
                665             670                 675
ASP ARG THR GLU CYS PHE ILE THR GLY TRP GLY GLU THR GLN GLY
                680             685                 690
THR PHE GLY ALA GLY LEU LEU LYS GLU ALA GLN LEU PRO VAL ILE
                695             700                 705
GLU ASN LYS VAL CYS ASN ARG TYR GLU PHE LEU ASN GLY ARG VAL
                710             715                 720
GLN SER THR GLU LEU CYS ALA GLY HIS LEU ALA GLY GLY THR ASP
                725             730                 735
SER CYS GLN GLY ASP SER GLY GLY PRO LEU VAL CYS PHE GLU LYS
                740             745                 750
ASP LYS TYR ILE LEU GLN GLY VAL THR SER TRP GLY LEU GLY CYS
                755             760                 765
ALA ARG PRO ASN LYS PRO GLY VAL TYR VAL ARG VAL SER ARG PHE
                770             775                 780
VAL THR TRP ILE GLU GLY VAL MET ARG ASN ASN
                785             790
```

Sequence alignment:

- Human (SEQ ID NO:2)
- Mouse (SEQ ID NO:8)
- Monkey (SEQ ID NO:9)
- Bovine (SEQ ID NO:10)
- Porcine (SEQ ID NO:11)

Positions 1–10:

| | 1 | 2 | 3 | 4 | 5 | 6 | 7 | 8 | 9 | 10 |
|---|---|---|---|---|---|---|---|---|---|---|
| Human | VAL | ALA | PRO | PRO | PRO | VAL | VAL | LEU | LEU | PRO |
| Mouse | --- | GLU | --- | --- | THR | --- | SER | GLN | GLU | --- |
| Monkey | ALA | --- | --- | --- | --- | ooo | ooo | ALA | GLN | --- |
| Bovine | PRO | --- | ALA | --- | --- | ooo | ooo | ILE | ALA | --- |
| Porcine | THR | ASN | PHE | --- | --- | ALA | ILE | ALA | GLN | VAL |

Positions 11–20:

| | 11 | 12 | 13 | 14 | 15 | 16 | 17 | 18 | 19 | 20 |
|---|---|---|---|---|---|---|---|---|---|---|
| Human | ASP | VAL | GLU | THR | PRO | SER | GLU | ASP | VAL | CYS |
| Mouse | SER | GLY | PRO | SER | ASP | --- | --- | --- | --- | --- |
| Monkey | --- | ALA | --- | --- | --- | --- | --- | --- | --- | --- |
| Bovine | GLY | --- | --- | ASN | --- | --- | --- | PRO | --- | --- |
| Porcine | SER | --- | --- | ASP | LEU | --- | --- | --- | --- | --- |

Positions 21–35:

| | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|
| Human | MET | PHE | GLY | ASN | GLY | LYS | GLY | TYR | ARG | GLY | LYS | ARG | ALA | THR | THR |
| Mouse | --- | TYR | --- | --- | --- | --- | --- | --- | --- | --- | --- | THR | --- | --- | VAL |
| Monkey | --- | --- | --- | --- | --- | ASP | --- | --- | --- | --- | --- | LYS | --- | --- | --- |
| Bovine | ILE | --- | --- | THR | --- | SER | --- | --- | --- | --- | --- | LYS | --- | --- | --- |
| Porcine | --- | --- | --- | --- | --- | ARG | --- | --- | --- | --- | --- | --- | --- | --- | --- |

Positions 36–50:

| | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|
| Human | VAL | THR | GLY | THR | PRO | CYS | GLN | ASP | TRP | ALA | ALA | GLN | GLU | PRO | HIS |
| Mouse | ALA | ALA | --- | --- | --- | --- | --- | GLY | --- | --- | --- | --- | --- | --- | --- |
| Monkey | --- | --- | --- | --- | --- | --- | --- | GLU | --- | --- | --- | --- | --- | --- | --- |
| Bovine | --- | ALA | --- | VAL | --- | --- | --- | GLU | --- | --- | --- | --- | --- | SER | --- |
| Porcine | --- | ALA | --- | VAL | --- | --- | --- | GLU | --- | --- | --- | --- | --- | HIS | --- |

FIG.2b

|  | 55 |  |  |  |  | 60 |  |  |  |  | 65 |  |  |
|---|---|---|---|---|---|---|---|---|---|---|---|---|---|---|
| Human | SER | ILE | PHE | THR | PRO | GLU | THR | ASN | PRO | ARG | ALA | GLY | LEU | GLU |
| Mouse | --- | --- | --- | --- | --- | GLN | --- | --- | --- | --- | --- | --- | --- | --- |
| Monkey | ARG | --- | --- | --- | --- | --- | --- | --- | --- | --- | --- | --- | --- | --- |
| Bovine | --- | --- | --- | --- | --- | --- | --- | --- | --- | GLN | SER | --- | --- | --- |
| Porcine | --- | --- | --- | --- | --- | --- | --- | --- | --- | --- | --- | --- | --- | --- |

|  |  |  |  | 70 |  |  |  |  | 75 |  |  |  |  | 80 |
|---|---|---|---|---|---|---|---|---|---|---|---|---|---|---|
| Human | LYS | ASN | TYR | CYS | ARG | ASN | PRO | ASP | GLY | ASP | VAL | GLY | GLY | PRO |
| Mouse | --- | --- | --- | --- | --- | --- | --- | --- | --- | --- | --- | ASN | --- | --- |
| Monkey | ARG | --- | --- | --- | --- | --- | --- | --- | --- | --- | --- | --- | --- | --- |
| Bovine | --- | --- | --- | --- | --- | --- | --- | --- | --- | --- | --- | ASN | --- | --- |
| Porcine | --- | --- | --- | --- | --- | --- | --- | --- | --- | ASP | ASN | --- | --- | --- |

|  |  |  |  |  | 85 |  |  |  |  | 90 |  |  |  |  |
|---|---|---|---|---|---|---|---|---|---|---|---|---|---|---|
| Human | TRP | CYS | TYR | THR | THR | ASN | PRO | ARG | LYS | LEU | TYR | ASP | TYR | CYS |
| Mouse | --- | --- | --- | --- | --- | --- | --- | --- | --- | --- | PHE | --- | --- | --- |
| Monkey | --- | --- | --- | --- | MET | --- | --- | --- | --- | --- | --- | --- | --- | --- |
| Bovine | --- | --- | --- | --- | --- | --- | --- | --- | --- | --- | PHE | --- | --- | --- |
| Porcine | --- | --- | --- | --- | --- | --- | --- | GLN | --- | --- | PHE | --- | --- | --- |

|  | 95 |  |  |  |  | 100 |  | 101 |
|---|---|---|---|---|---|---|---|---|
| Human | ASP | VAL | PRO | GLN | CYS | ALA | 000 | ALA |
| Mouse | --- | ILE | --- | LEU | --- | --- | --- | --- |
| Monkey | --- | --- | --- | --- | --- | SER | --- | --- |
| Bovine | --- | --- | --- | --- | --- | GLU | 000 | 000 |
| Porcine | --- | --- | --- | --- | --- | VAL | 000 | THR |

| INHIBITORY ACTIVITY OF BCE CELL PROLIFERATION ||
|---|---|
| FRAGMENTS | ED50 (nM) |
| KRINGLE 1 | 320 |
| KRINGLE 2 | --- |
| KRINGLE 3 | 460 |
| KRINGLE 4 | --- |
| KRINGLE 5 | 0.300 |
| KRINGLES 2-3 | --- |
| KRINGLES 1-3 | 75 |
| KRINGLES 1-4 (ANGIOSTATIN) | 135 |

FIG.4c

| | | | | |
|---|---|---|---|---|
| 1 | CATCCTGGGA | TTGGGACCCA | CTTTCTGGGC | ACTGCTGGCC | AGTCCCAAAA |
| 51 | TGGAACATAA | GGAAGTGGTT | CTTCTACTTC | TTTTATTTCT | GAAATCAGGT |
| 101 | CAAGGAGAGC | CTCTGGATGA | CTATGTGAAT | ACCCAGGGGG | CTTCACTGTT |
| 151 | CAGTGTCACT | AAGAAGCAGC | TGGGAGCAGG | AAGTATAGAA | GAATGTGCAG |
| 201 | CAAAATGTGA | GGAGGACGAA | GAATTCACCT | GCAGGGCATT | CCAATATCAC |
| 251 | AGTAAAGAGC | AACAATGTGT | GATAATGGCT | GAAAACAGGA | AGTCCTCCAT |
| 301 | AATCATTAGG | ATGAGAGATG | TAGTTTTATT | TGAAAAGAAA | GTGTATCTCT |
| 351 | CAGAGTGCAA | GACTGGGAAT | GGAAAGAACT | ACAGAGGGAC | GATGTCCAAA |
| 401 | ACAAAAAATG | GCATCACCTG | TCAAAAATGG | AGTTCCACTT | CTCCCCACAG |
| 451 | ACCTAGATTC | TCACCTGCTA | CACACCCCTC | AGAGGGACTG | GAGGAGAACT |
| 501 | ACTGCAGGAA | TCCAGACAAC | GATCCGCAGG | GGCCCTGGTG | CTATACTACT |
| 551 | GATCCAGAAA | AGAGATATGA | CTACTGCGAC | ATTCTTGAGT | GTGAAGAGGA |
| 601 | ATGTATGCAT | TGCAGTGGAG | AAAACTATGA | CGGCAAAATT | TCCAAGACCA |
| 651 | TGTCTGGACT | GGAATGCCAG | GCCTGGGACT | CTCAGAGCCC | ACACGCTCAT |
| 701 | GGATACATTC | CTTCCAAATT | TCCAAACAAG | AACCTGAAGA | AGAATTACTG |
| 751 | TCGTAACCCC | GATAGGGAGC | TGCGGCCTTG | GTGTTTCACC | ACCGACCCCA |
| 801 | ACAAGCGCTG | GGAACTTTGT | GACATCCCCC | GCTGCACAAC | ACCTCCACCA |
| 851 | TCTTCTGGTC | CCACCTACCA | GTGTCTGAAG | GGAACAGGTG | AAAACTATCG |
| 901 | CGGGAATGTG | GCTGTTACCG | TGTCCGGGCA | CACCTGTCAG | CACTGGAGTG |
| 951 | CACAGACCCC | TCACACACAT | AACAGGACAC | CAGAAAACTT | CCCCTGCAAA |
| 1001 | AATTTGGATG | AAAACTACTG | CCGCAATCCT | GACGGAAAAA | GGGCCCCATG |
| 1051 | GTGCCATACA | ACCAACAGCC | AAGTGCGGTG | GGAGTACTGT | AAGATACCGT |
| 1101 | CCTGTGACTC | CTCCCCAGTA | TCCACGGAAC | AATTGGCTCC | CACAGCACCA |
| 1151 | CCTGAGCTAA | CCCCTGTGGT | CCAGGACTGC | TACCATGGTG | ATGGACAGAG |
| 1201 | CTACCGAGGC | ACATCCTCCA | CCACCACCAC | AGGAAAGAAG | TGTCAGTCTT |
| 1251 | GGTCATCTAT | GACACCACAC | CGGCACCAGA | AGACCCCAGA | AAACTACCCA |

(SEQ ID NO:12)

FIG. 6a

```
1301  AATGCTGGCC TGACAATGAA CTACTGCAGG AATCCAGATG CCGATAAAGG
1351  CCCCTGGTGT TTTACCACAG ACCCCAGCGT CAGGTGGGAG TACTGCAACC
1401  TGAAAAAATG CTCAGGAACA GAAGCGAGTG TTGTAGCACC TCCGCCTGTT
1451  GTCCTGCTTC CAGATGTAGA GACTCCTTCC GAAGAAGACT GTATGTTTGG
1501  GAATGGGAAA GGATACCGAG GCAAGAGGGC GACCACTGTT ACTGGGACGC
1551  CATGCCAGGA CTGGGCTGCC CAGGAGCCCC ATAGACACAG CATTTTCACT
1601  CCAGAGACAA ATCCACGGGC GGGTCTGGAA AAAAATTACT GCCGTAACCC
1651  TGATGGTGAT GTAGGTGGTC CCTGGTGCTA CACGACAAAT CCAAGAAAAC
1701  TTTACGACTA CTGTGATGTC CCTCAGTGTG CGGCCCCTTC ATTTGATTGT
1751  GGGAAGCCTC AAGTGGAGCC GAAGAAATGT CCTGGAAGGG TTGTAGGGGG
1801  GTGTGTGGCC CACCCACATT CCTGGCCCTG GCAAGTCAGT CTTAGAACAA
1851  GGTTTGGAAT GCACTTCTGT GGAGGCACCT TGATATCCCC AGAGTGGGTG
1901  TTGACTGCTG CCCACTGCTT GGAGAAGTCC CCAAGGCCTT CATCCTACAA
1951  GGTCATCCTG GGTGCACACC AAGAAGTGAA TCTCGAACCG CATGTTCAGG
2001  AAATAGAAGT GTCTAGGCTG TTCTTGGAGC CCACACGAAA AGATATTGCC
2051  TTGCTAAAGC TAAGCAGTCC TGCCGTCATC ACTGACAAAG TAATCCCAGC
2101  TTGTCTGCCA TCCCCAAATT ATGTGGTCGC TGACCGGACC GAATGTTTCG
2151  TCACTGGCTG GGAGAAACC CAAGGTACTT TTGGAGCTGG CCTTCTCAAG
2201  GAAGCCCAGC TCCCTGTGAT TGAGAATAAA GTGTGCAATC GCTATGAGTT
2251  TCTGAATGGA AGAGTCCAAT CCACCGAACT CTGTGCTGGG CATTTGGCCG
2301  GAGGCACTGA CAGTTGCCAG GGTGACAGTG GAGGTCCTCT GGTTTGCTTC
2351  GAGAAGGACA AATACATTTT ACAAGGAGTC ACTTCTTGGG GTCTTGGCTG
2401  TGCACGCCCC AATAAGCCTG GTGTCTATGT TCGTGTTTCA AGGTTTGTTA
2451  CTTGGATTGA GGGAGTGATG AGAAATAATT AATTGGACGG GAGACAG
```

FIG.6b

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 791 amino acids
( B ) TYPE: amino acid
( D ) TOPOLOGY: linear ( i i ) MOLECULE TYPE:
( A ) DESCRIPTION: protein ( x i ) SEQUENCE DESCRIPTION: SEQ ID NO:1:

```
Glu Pro Leu Asp Asp Tyr Val Asn Thr Gln Gly Ala Ser Leu Phe Ser
 1               5                  10                  15
Val Thr Lys Lys Gln Leu Gly Ala Gly Ser Ile Glu Glu Cys Ala Ala
                20                  25                  30
Lys Cys Glu Glu Asp Glu Glu Phe Thr Cys Arg Ala Phe Gln Tyr His
            35                  40                  45
Ser Lys Glu Gln Gln Cys Val Ile Met Ala Glu Asn Arg Ser Ser Ser
        50                  55                  60
Ile Ile Ile Arg Met Arg Asp Val Val Leu Phe Glu Lys Lys Val Tyr
65                  70                  75                  80
Leu Ser Glu Cys Lys Thr Gly Asn Gly Lys Asn Tyr Arg Gly Thr Met
                85                  90                  95
Ser Lys Thr Lys Asn Gly Ile Thr Cys Gln Lys Trp Ser Ser Thr Ser
            100                 105                 110
Pro His Arg Pro Arg Phe Ser Pro Ala Thr His Pro Ser Glu Gly Leu
        115                 120                 125
Glu Glu Asn Tyr Cys Arg Asn Pro Asp Asn Asp Pro Gln Gly Pro Trp
    130                 135                 140
Cys Tyr Thr Thr Asp Pro Glu Lys Arg Tyr Asp Tyr Cys Asp Ile Leu
145                 150                 155                 160
Glu Cys Gln Glu Glu Cys Met His Cys Ser Gly Glu Asn Tyr Asp Gly
                165                 170                 175
Lys Ile Ser Lys Thr Met Ser Gly Leu Glu Cys Gln Ala Trp Asp Ser
            180                 185                 190
Gln Ser Pro His Ala His Gly Tyr Ile Pro Ser Lys Phe Pro Asn Lys
        195                 200                 205
Asn Leu Lys Lys Asn Tyr Cys Arg Asn Pro Asp Arg Glu Leu Arg Pro
    210                 215                 220
Trp Cys Phe Thr Thr Asp Pro Asn Lys Arg Trp Glu Leu Cys Asp Ile
225                 230                 235                 240
Pro Arg Cys Thr Thr Pro Pro Pro Ser Ser Gly Pro Thr Tyr Gln Cys
                245                 250                 255
Leu Lys Gly Thr Gly Glu Asn Tyr Arg Gly Asn Val Ala Val Thr Val
            260                 265                 270
Ser Gly His Thr Cys Gln His Trp Ser Ala Gln Thr Pro His Thr His
        275                 280                 285
Asn Arg Thr Pro Glu Asn Phe Pro Cys Lys Asn Leu Asp Glu Asn Tyr
    290                 295                 300
Cys Arg Asn Pro Asp Gly Lys Arg Ala Pro Trp Cys His Thr Thr Asn
305                 310                 315                 320
```

| Ser | Gln | Val | Arg | Trp | Glu | Tyr | Cys | Lys | Ile | Pro | Ser | Cys | Asp | Ser | Ser |
| | | | | 325 | | | | 330 | | | | | | 335 | |
| Pro | Val | Ser | Thr | Glu | Gln | Leu | Ala | Pro | Thr | Ala | Pro | Pro | Glu | Leu | Thr |
| | | | 340 | | | | | 345 | | | | | 350 | | |
| Pro | Val | Val | Gln | Asp | Cys | Tyr | His | Gly | Asp | Gly | Gln | Ser | Tyr | Arg | Gly |
| | | | 355 | | | | | 360 | | | | | 365 | | |
| Thr | Ser | Ser | Thr | Thr | Thr | Thr | Gly | Lys | Lys | Cys | Gln | Ser | Trp | Ser | Ser |
| | 370 | | | | | | 375 | | | | | 380 | | | |
| Met | Thr | Pro | His | Arg | His | Gln | Lys | Thr | Pro | Glu | Asn | Tyr | Pro | Asn | Ala |
| 385 | | | | | 390 | | | | | 395 | | | | | 400 |
| Gly | Leu | Thr | Met | Asn | Tyr | Cys | Arg | Asn | Pro | Asp | Ala | Asp | Lys | Gly | Pro |
| | | | | 405 | | | | | 410 | | | | | 415 | |
| Trp | Cys | Phe | Thr | Thr | Asp | Pro | Ser | Val | Arg | Trp | Glu | Tyr | Cys | Asn | Leu |
| | | | 420 | | | | | 425 | | | | | 430 | | |
| Lys | Lys | Cys | Ser | Gly | Thr | Glu | Ala | Ser | Val | Val | Ala | Pro | Pro | Pro | Val |
| | | 435 | | | | | 440 | | | | | 445 | | | |
| Val | Leu | Leu | Pro | Asp | Val | Glu | Thr | Pro | Ser | Glu | Glu | Asp | Cys | Met | Phe |
| | 450 | | | | | 455 | | | | | 460 | | | | |
| Gly | Asn | Gly | Lys | Gly | Tyr | Arg | Gly | Lys | Arg | Ala | Thr | Thr | Val | Thr | Gly |
| 465 | | | | | 470 | | | | | 475 | | | | | 480 |
| Thr | Pro | Cys | Gln | Asp | Trp | Ala | Ala | Gln | Glu | Pro | His | Arg | His | Ser | Ile |
| | | | | 485 | | | | | 490 | | | | | 495 | |
| Phe | Thr | Pro | Glu | Thr | Asn | Pro | Arg | Ala | Gly | Leu | Glu | Lys | Asn | Tyr | Cys |
| | | | 500 | | | | | 505 | | | | | 510 | | |
| Arg | Asn | Pro | Asp | Gly | Asp | Val | Gly | Gly | Pro | Trp | Cys | Tyr | Thr | Thr | Asn |
| | | 515 | | | | | 520 | | | | | 525 | | | |
| Pro | Arg | Ser | Leu | Tyr | Asp | Tyr | Cys | Asp | Val | Pro | Gln | Cys | Ala | Ala | Pro |
| | 530 | | | | | 535 | | | | | 540 | | | | |
| Ser | Phe | Asp | Cys | Gly | Lys | Pro | Gln | Val | Glu | Pro | Lys | Lys | Cys | Pro | Gly |
| 545 | | | | | 550 | | | | | 555 | | | | | 560 |
| Arg | Val | Val | Gly | Gly | Cys | Val | Ala | His | Pro | His | Ser | Trp | Pro | Trp | Gln |
| | | | | 565 | | | | | 570 | | | | | 575 | |
| Val | Ser | Leu | Arg | Thr | Arg | Phe | Gly | Met | His | Phe | Cys | Gly | Gly | Thr | Leu |
| | | | 580 | | | | | 585 | | | | | 590 | | |
| Ile | Ser | Pro | Glu | Trp | Val | Leu | Thr | Ala | Ala | His | Cys | Leu | Glu | Lys | Ser |
| | | 595 | | | | | 600 | | | | | 605 | | | |
| Pro | Arg | Pro | Ser | Ser | Tyr | Lys | Val | Ile | Leu | Gly | Ala | His | Gln | Glu | Val |
| | 610 | | | | | 615 | | | | | 620 | | | | |
| Asn | Leu | Glu | Pro | His | Val | Gln | Glu | Ile | Glu | Val | Ser | Arg | Leu | Phe | Leu |
| 625 | | | | | 630 | | | | | 635 | | | | | 640 |
| Glu | Pro | Thr | Arg | Ser | Asp | Ile | Ala | Leu | Leu | Lys | Leu | Ser | Ser | Pro | Ala |
| | | | | 645 | | | | | 650 | | | | | 655 | |
| Val | Ile | Thr | Asp | Lys | Val | Ile | Pro | Ala | Cys | Leu | Pro | Ser | Pro | Asn | Tyr |
| | | | 660 | | | | | 665 | | | | | 670 | | |
| Val | Val | Ala | Asp | Arg | Thr | Glu | Cys | Phe | Ile | Thr | Gly | Trp | Gly | Glu | Thr |
| | | 675 | | | | | 680 | | | | | 685 | | | |
| Gln | Gly | Thr | Phe | Gly | Ala | Gly | Leu | Leu | Lys | Glu | Ala | Gln | Leu | Pro | Val |
| | 690 | | | | | 695 | | | | | 700 | | | | |
| Ile | Glu | Asn | Lys | Val | Cys | Asn | Arg | Tyr | Glu | Phe | Leu | Asn | Gly | Arg | Val |
| 705 | | | | | 710 | | | | | 715 | | | | | 720 |
| Gln | Ser | Thr | Glu | Leu | Cys | Ala | Gly | His | Leu | Ala | Gly | Gly | Thr | Asp | Ser |
| | | | | 725 | | | | | 730 | | | | | 735 | |
| Cys | Gln | Gly | Asp | Ser | Gly | Gly | Pro | Leu | Val | Cys | Phe | Glu | Lys | Asp | Lys |
| | | | 740 | | | | | 745 | | | | | 750 | | |

| Tyr | Ile | Leu | Gln | Gly | Val | Thr | Ser | Trp | Gly | Leu | Gly | Cys | Ala | Arg | Pro |
|    |    | 755 |    |    |    |    | 760 |    |    |    |    | 765 |    |    |    |

| Asn | Lys | Pro | Gly | Val | Tyr | Val | Arg | Val | Ser | Arg | Phe | Val | Thr | Trp | Ile |
|    | 770 |    |    |    |    | 775 |    |    |    |    | 780 |    |    |    |    |

| Glu | Gly | Val | Met | Arg | Asn | Asn |
| 785 |    |    |    |    | 790 |    |

( 2 ) INFORMATION FOR SEQ ID NO:2:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( x i ) SEQUENCE DESCRIPTION: SEQ ID NO:2:

| Val | Ala | Pro | Pro | Pro | Val | Val | Leu | Leu | Pro | Asp | Val | Glu | Thr | Pro | Ser |
| 1   |    |    |    | 5   |    |    |    |    | 10  |    |    |    |    | 15  |    |

| Glu | Glu | Asp | Cys | Met | Phe | Gly | Asn | Gly | Lys | Gly | Tyr | Arg | Gly | Lys | Arg |
|    |    |    | 20  |    |    |    |    | 25  |    |    |    |    | 30  |    |    |

| Ala | Thr | Thr | Val | Thr | Gly | Thr | Pro | Cys | Gln | Asp | Trp | Ala | Ala | Gln | Glu |
|    |    | 35  |    |    |    |    | 40  |    |    |    |    | 45  |    |    |    |

| Pro | His | Arg | His | Ser | Ile | Phe | Thr | Pro | Glu | Thr | Asn | Pro | Arg | Ala | Gly |
|    | 50  |    |    |    |    | 55  |    |    |    |    | 60  |    |    |    |    |

| Leu | Glu | Lys | Asn | Tyr | Cys | Arg | Asn | Pro | Asp | Gly | Asp | Val | Gly | Gly | Pro |
| 65  |    |    |    |    | 70  |    |    |    |    | 75  |    |    |    |    | 80  |

| Trp | Cys | Tyr | Thr | Thr | Asn | Pro | Arg | Ser | Leu | Tyr | Asp | Tyr | Cys | Asp | Val |
|    |    |    |    | 85  |    |    |    |    | 90  |    |    |    |    | 95  |    |

| Pro | Gln | Cys | Ala | Ala |
|    |    |    | 100 |    |

( 2 ) INFORMATION FOR SEQ ID NO:3:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( x i ) SEQUENCE DESCRIPTION: SEQ ID NO:3:

| Val | Leu | Leu | Pro | Asp | Val | Glu | Thr | Pro | Ser | Glu | Glu | Asp | Cys | Met | Phe |
| 1   |    |    |    | 5   |    |    |    |    | 10  |    |    |    |    | 15  |    |

| Gly | Asn | Gly | Lys | Gly | Tyr | Arg | Gly | Lys | Arg | Ala | Thr | Thr | Val | Thr | Gly |
|    |    |    | 20  |    |    |    |    | 25  |    |    |    |    | 30  |    |    |

| Thr | Pro | Cys | Gln | Asp | Trp | Ala | Ala | Gln | Glu | Pro | His | Arg | His | Ser | Ile |
|    |    | 35  |    |    |    |    | 40  |    |    |    |    | 45  |    |    |    |

| Phe | Thr | Pro | Glu | Thr | Asn | Pro | Arg | Ala | Gly | Leu | Glu | Lys | Asn | Tyr | Cys |
|    | 50  |    |    |    |    | 55  |    |    |    |    | 60  |    |    |    |    |

| Arg | Asn | Pro | Asp | Gly | Asp | Val | Gly | Gly | Pro | Trp | Cys | Tyr | Thr | Thr | Asn |
| 65  |    |    |    |    | 70  |    |    |    |    | 75  |    |    |    |    | 80  |

| Pro | Arg | Ser | Leu | Tyr | Asp | Tyr | Cys | Asp | Val | Pro | Gln | Cys | Ala | Ala |
|    |    |    |    | 85  |    |    |    |    | 90  |    |    |    |    | 95  |

( 2 ) INFORMATION FOR SEQ ID NO:4:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( x i ) SEQUENCE DESCRIPTION: SEQ ID NO:4:

```
Val Glu Thr Pro Ser Glu Glu Asp Cys Met Phe Gly Asn Gly Lys Gly
 1               5                  10                      15

Tyr Arg Gly Lys Arg Ala Thr Thr Val Thr Gly Thr Pro Cys Gln Asp
             20                  25                  30

Trp Ala Ala Gln Glu Pro His Arg His Ser Ile Phe Thr Pro Glu Thr
             35              40                  45

Asn Pro Arg Ala Gly Leu Glu Lys Asn Tyr Cys Arg Asn Pro Asp Gly
         50              55                  60

Asp Val Gly Gly Pro Trp Cys Tyr Thr Thr Asn Pro Arg Ser Leu Tyr
 65                      70                  75                  80

Asp Tyr Cys Asp Val Pro Gln Cys Ala Ala
                 85                  90
```

( 2 ) INFORMATION FOR SEQ ID NO:5:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( x i ) SEQUENCE DESCRIPTION: SEQ ID NO:5:

```
Val Ala Pro Pro Pro Val Val Leu Leu Pro Asp Val Glu Thr Pro Ser
 1               5                  10                      15

Glu Glu Asp Cys Met Phe Gly Asn Gly Lys Gly Tyr Arg Gly Lys Arg
             20                  25                  30

Ala Thr Thr Val Thr Gly Thr Pro Cys Gln Asp Trp Ala Ala Gln Glu
             35              40                  45

Pro His Arg His Ser Ile Phe Thr Pro Glu Thr Asn Pro Arg Ala Gly
     50                  55                  60

Leu Glu Lys Asn Tyr Cys Arg Asn Pro Asp Gly Asp Val Gly Gly Pro
 65                      70                  75                  80

Trp Cys Tyr Thr Thr Asn Pro Arg Ser Leu Tyr Asp Tyr Cys Asp Val
                 85                  90                  95

Pro Gln Cys Ala Ala Pro Ser Phe
                100
```

( 2 ) INFORMATION FOR SEQ ID NO:6:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( x i ) SEQUENCE DESCRIPTION: SEQ ID NO:6:

| Val | Leu | Leu | Pro | Asp | Val | Glu | Thr | Pro | Ser | Glu | Glu | Asp | Cys | Met | Phe |
|---|---|---|---|---|---|---|---|---|---|---|---|---|---|---|---|
| 1 | | | | 5 | | | | | 10 | | | | | 15 | |

| Gly | Asn | Gly | Lys | Gly | Tyr | Arg | Gly | Lys | Arg | Ala | Thr | Thr | Val | Thr | Gly |
|---|---|---|---|---|---|---|---|---|---|---|---|---|---|---|---|
| | | | 20 | | | | | 25 | | | | | 30 | | |

| Thr | Pro | Cys | Gln | Asp | Trp | Ala | Ala | Gln | Glu | Pro | His | Arg | His | Ser | Ile |
|---|---|---|---|---|---|---|---|---|---|---|---|---|---|---|---|
| | | 35 | | | | | 40 | | | | | 45 | | | |

| Phe | Thr | Pro | Glu | Thr | Asn | Pro | Arg | Ala | Gly | Leu | Glu | Lys | Asn | Tyr | Cys |
|---|---|---|---|---|---|---|---|---|---|---|---|---|---|---|---|
| | 50 | | | | | 55 | | | | | 60 | | | | |

| Arg | Asn | Pro | Asp | Gly | Asp | Val | Gly | Gly | Pro | Trp | Cys | Tyr | Thr | Thr | Asn |
|---|---|---|---|---|---|---|---|---|---|---|---|---|---|---|---|
| 65 | | | | | 70 | | | | | 75 | | | | | 80 |

| Pro | Arg | Ser | Leu | Tyr | Asp | Tyr | Cys | Asp | Val | Pro | Gln | Cys | Ala | Ala | Pro |
|---|---|---|---|---|---|---|---|---|---|---|---|---|---|---|---|
| | | | | 85 | | | | | 90 | | | | | 95 | |

| Ser | Phe |
|---|---|

( 2 ) INFORMATION FOR SEQ ID NO:7:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( x i ) SEQUENCE DESCRIPTION: SEQ ID NO:7:

| Val | Glu | Thr | Pro | Ser | Glu | Glu | Asp | Cys | Met | Phe | Gly | Asn | Gly | Lys | Gly |
|---|---|---|---|---|---|---|---|---|---|---|---|---|---|---|---|
| 1 | | | | 5 | | | | | 10 | | | | | 15 | |

| Tyr | Arg | Gly | Lys | Arg | Ala | Thr | Thr | Val | Thr | Gly | Thr | Pro | Cys | Gln | Asp |
|---|---|---|---|---|---|---|---|---|---|---|---|---|---|---|---|
| | | | 20 | | | | | 25 | | | | | 30 | | |

| Trp | Ala | Ala | Gln | Glu | Pro | His | Arg | His | Ser | Ile | Phe | Thr | Pro | Glu | Thr |
|---|---|---|---|---|---|---|---|---|---|---|---|---|---|---|---|
| | | | 35 | | | | | 40 | | | | | 45 | | |

| Asn | Pro | Arg | Ala | Gly | Leu | Glu | Lys | Asn | Tyr | Cys | Arg | Asn | Pro | Asp | Gly |
|---|---|---|---|---|---|---|---|---|---|---|---|---|---|---|---|
| | 50 | | | | | 55 | | | | | 60 | | | | |

| Asp | Val | Gly | Gly | Pro | Trp | Cys | Tyr | Thr | Thr | Asn | Pro | Arg | Ser | Leu | Tyr |
|---|---|---|---|---|---|---|---|---|---|---|---|---|---|---|---|
| 65 | | | | | 70 | | | | | 75 | | | | | 80 |

| Asp | Tyr | Cys | Asp | Val | Pro | Gln | Cys | Ala | Ala | Pro | Ser | Phe |
|---|---|---|---|---|---|---|---|---|---|---|---|---|
| | | | | 85 | | | | | 90 | | | |

( 2 ) INFORMATION FOR SEQ ID NO:8:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( i x ) FEATURE:
        ( A ) NAME/KEY: mouse sequence ( x i ) SEQUENCE DESCRIPTION: SEQ ID NO:8:

| Val | Glu | Leu | Pro | Thr | Val | Ser | Gln | Glu | Pro | Ser | Gly | Pro | Ser | Asp | Ser |
|---|---|---|---|---|---|---|---|---|---|---|---|---|---|---|---|
| 1 | | | | 5 | | | | | 10 | | | | | 15 | |

| Glu | Thr | Asp | Cys | Met | Tyr | Gly | Asn | Asp | Lys | Asp | Tyr | Arg | Thr | Lys | Thr |
|---|---|---|---|---|---|---|---|---|---|---|---|---|---|---|---|
| | | | 20 | | | | | 25 | | | | | 30 | | |

```
Ala  Val  Ala  Ala  Ala  Gly  Thr  Pro  Gly  Gln  Gly  Trp  Ala  Ala  Gln  Glu
     35                      40                           45

Pro  His  Arg  His  Ser  Ile  Phe  Thr  Pro  Gln  Thr  Asn  Pro  Arg  Ala  Gly
     50                      55                           60

Leu  Glu  Lys  Asn  Tyr  Cys  Arg  Asn  Pro  Asp  Gly  Asp  Val  Asn  Gly  Pro
65                       70                      75                           80

Trp  Cys  Tyr  Thr  Thr  Asn  Pro  Arg  Ser  Leu  Tyr  Asp  Tyr  Cys  Asp  Ile
               85                           90                      95

Pro  Leu  Cys  Ala  Ser  Ala
               100
```

( 2 ) INFORMATION FOR SEQ ID NO:9:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( i x ) FEATURE:
        ( A ) NAME/KEY: monkey sequence ( x i ) SEQUENCE DESCRIPTION: SEQ ID NO:9:

```
Ala  Ala  Pro  Pro  Pro  Val  Ala  Gln  Leu  Pro  Asp  Ala  Glu  Thr  Pro  Ser
1                        5                        10                      15

Glu  Glu  Asp  Cys  Met  Phe  Gly  Asn  Gly  Lys  Gly  Tyr  Arg  Gly  Lys  Lys
               20                      25                      30

Ala  Thr  Thr  Val  Thr  Gly  Thr  Pro  Cys  Gln  Asp  Trp  Ala  Ala  Gln  Glu
     35                      40                           45

Pro  His  Ser  His  Arg  Ile  Phe  Thr  Pro  Glu  Thr  Asn  Pro  Arg  Ala  Gly
     50                      55                           60

Leu  Glu  Lys  Asn  Tyr  Cys  Arg  Asn  Pro  Asp  Gly  Asp  Val  Gly  Gly  Pro
65                       70                      75                           80

Trp  Cys  Tyr  Thr  Thr  Asn  Pro  Arg  Ser  Leu  Phe  Asp  Tyr  Cys  Asp  Val
               85                           90                      95

Pro  Gln  Cys  Ala
               100
```

( 2 ) INFORMATION FOR SEQ ID NO:10:

( i ) SEQUENCE CHARACTERISTICS:
        ( A ) LENGTH: 97 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( i x ) FEATURE:
        ( A ) NAME/KEY: bovine sequence ( x i ) SEQUENCE DESCRIPTION: SEQ ID NO:10:

```
Pro  Ala  Ala  Pro  Gln  Ala  Pro  Gly  Val  Glu  Asn  Pro  Pro  Glu  Ala  Asp
1                        5                        10                      15

Cys  Met  Ile  Gly  Thr  Gly  Lys  Ser  Tyr  Arg  Gly  Lys  Lys  Ala  Thr  Thr
               20                      25                      30

Val  Ala  Gly  Val  Pro  Cys  Gln  Glu  Trp  Ala  Ala  Gln  Glu  Pro  His  His
     35                      40                           45
```

His Ser Ile Phe Thr Pro Glu Thr Asn Pro Gln Ser Gly Leu Glu Arg
          50                  55                  60

Asn Tyr Cys Arg Asn Pro Asp Gly Asp Val Asn Gly Pro Trp Cys Tyr
 65                  70                  75                  80

Thr Met Asn Pro Arg Ser Leu Phe Asp Tyr Cys Asp Val Pro Gln Cys
                  85                  90                  95

Glu ( 2 ) INFORMATION FOR SEQ ID NO:11:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE:
        ( A ) DESCRIPTION: protein ( v ) FRAGMENT TYPE: internal ( i x ) FEATURE:
        ( A ) NAME/KEY: porcine sequence ( x i ) SEQUENCE DESCRIPTION: SEQ ID NO:11:

Thr Asn Phe Pro Ala Ile Ala Gln Val Pro Ser Val Glu Asp Leu Ser
 1                   5                  10                  15

Glu Glu Asp Cys Met Phe Gly Asn Gly Lys Arg Tyr Arg Gly Lys Arg
                  20                  25                  30

Ala Thr Thr Val Ala Gly Val Pro Cys Gln Glu Trp Ala Ala Gln Glu
                  35                  40                  45

Pro His Arg His Ser Ile Phe Thr Pro Glu Thr Asn Pro Arg Ala Gly
          50                  55                  60

Leu Glu Lys Asn Tyr Cys Arg Asn Pro Asp Gly Asp Asp Asn Gly Pro
 65                  70                  75                  80

Trp Cys Tyr Thr Thr Asn Pro Gln Lys Leu Phe Asp Tyr Cys Asp Val
                  85                  90                  95

Pro Gln Cys Val Thr
                 100

( 2 ) INFORMATION FOR SEQ ID NO:12:

( i ) SEQUENCE CHARACTERISTICS:
        ( A ) LENGTH: 2497 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:12:

```
CATCCTGGGA TTGGGACCCA CTTTCTGGGC ACTGCTGGCC AGTCCCAAAA TGGAACATAA      60
GGAAGTGGTT CTTCTACTTC TTTATTTCT  GAAATCAGGT CAAGGAGAGC CTCTGGATGA     120
CTATGTGAAT ACCCAGGGGG CTTCACTGTT CAGTGTCACT AAGAAGCAGC TGGGAGCAGG     180
AAGTATAGAA GAATGTGCAG CAAAATGTGA GGAGGACGAA GAATTCACCT GCAGGGCATT     240
CCAATATCAC AGTAAAGAGC AACAATGTGT GATAATGGCT GAAAACAGGA AGTCCTCCAT     300
AATCATTAGG ATGAGAGATG TAGTTTTATT TGAAAAGAAA GTGTATCTCT CAGAGTGCAA     360
GACTGGGAAT GGAAAGAACT ACAGAGGGAC GATGTCCAAA ACAAAAAATG GCATCACCTG     420
TCAAAAATGG AGTTCCACTT CTCCCCACAG ACCTAGATTC TCACCTGCTA CACACCCCTC     480
```

| | | | | | |
|---|---|---|---|---|---|
| AGAGGGACTG | GAGGAGAACT | ACTGCAGGAA | TCCAGACAAC | GATCCGCAGG | GGCCCTGGTG | 540 |
| CTATACTACT | GATCCAGAAA | AGAGATATGA | CTACTGCGAC | ATTCTTGAGT | GTGAAGAGGA | 600 |
| ATGTATGCAT | TGCAGTGGAG | AAAACTATGA | CGGCAAAATT | TCCAAGACCA | TGTCTGGACT | 660 |
| GGAATGCCAG | GCCTGGGACT | CTCAGAGCCC | ACACGCTCAT | GGATACATTC | CTTCCAAATT | 720 |
| TCCAAACAAG | AACCTGAAGA | AGAATTACTG | TCGTAACCCC | GATAGGGAGC | TGCGGCCTTG | 780 |
| GTGTTTCACC | ACCGACCCCA | ACAAGCGCTG | GGAACTTTGT | GACATCCCCC | GCTGCACAAC | 840 |
| ACCTCCACCA | TCTTCTGGTC | CCACCTACCA | GTGTCTGAAG | GGAACAGGTG | AAAACTATCG | 900 |
| CGGGAATGTG | GCTGTTACCG | TGTCCGGGCA | CACCTGTCAG | CACTGGAGTG | CACAGACCCC | 960 |
| TCACACACAT | AACAGGACAC | CAGAAAACTT | CCCCTGCAAA | AATTTGGATG | AAAACTACTG | 1020 |
| CCGCAATCCT | GACGGAAAAA | GGGCCCCATG | GTGCCATACA | ACCAACAGCC | AAGTGCGGTG | 1080 |
| GGAGTACTGT | AAGATACCGT | CCTGTGACTC | CTCCCAGTA | TCCACGGAAC | AATTGGCTCC | 1140 |
| CACAGCACCA | CCTGAGCTAA | CCCCTGTGGT | CCAGGACTGC | TACCATGGTG | ATGGACAGAG | 1200 |
| CTACCGAGGC | ACATCCTCCA | CCACCACCAC | AGGAAAGAAG | TGTCAGTCTT | GGTCATCTAT | 1260 |
| GACACCACAC | CGGCACCAGA | AGACCCCAGA | AAACTACCCA | AATGCTGGCC | TGACAATGAA | 1320 |
| CTACTGCAGG | AATCCAGATG | CCGATAAAGG | CCCCTGGTGT | TTTACCACAG | ACCCCAGCGT | 1380 |
| CAGGTGGGAG | TACTGCAACC | TGAAAAAATG | CTCAGGAACA | GAAGCGAGTG | TTGTAGCACC | 1440 |
| TCCGCCTGTT | GTCCTGCTTC | CAGATGTAGA | GACTCCTTCC | GAAGAAGACT | GTATGTTTGG | 1500 |
| GAATGGGAAA | GGATACCGAG | GCAAGAGGGC | GACCACTGTT | ACTGGGACGC | CATGCCAGGA | 1560 |
| CTGGGCTGCC | CAGGAGCCCC | ATAGACACAG | CATTTCACT | CCAGAGACAA | ATCCACGGGC | 1620 |
| GGGTCTGGAA | AAAAATTACT | GCCGTAACCC | TGATGGTGAT | GTAGGTGGTC | CCTGGTGCTA | 1680 |
| CACGACAAAT | CCAAGAAAAC | TTTACGACTA | CTGTGATGTC | CCTCAGTGTG | CGGCCCCTTC | 1740 |
| ATTTGATTGT | GGGAAGCCTC | AAGTGGAGCC | GAAGAAATGT | CCTGGAAGGG | TTGTAGGGGG | 1800 |
| GTGTGTGGCC | CACCCACATT | CCTGGCCCTG | GCAAGTCAGT | CTTAGAACAA | GGTTTGGAAT | 1860 |
| GCACTTCTGT | GGAGGCACCT | TGATATCCCC | AGAGTGGGTG | TTGACTGCTG | CCCACTGCTT | 1920 |
| GGAGAAGTCC | CCAAGGCCTT | CATCCTACAA | GGTCATCCTG | GGTGCACACC | AAGAAGTGAA | 1980 |
| TCTCGAACCG | CATGTTCAGG | AAATAGAAGT | GTCTAGGCTG | TTCTTGGAGC | CCACACGAAA | 2040 |
| AGATATTGCC | TTGCTAAAGC | TAAGCAGTCC | TGCCGTCATC | ACTGACAAAG | TAATCCCAGC | 2100 |
| TTGTCTGCCA | TCCCCAAATT | ATGTGGTCGC | TGACCGGACC | GAATGTTTCG | TCACTGGCTG | 2160 |
| GGGAGAAACC | CAAGGTACTT | TTGGAGCTGG | CCTTCTCAAG | GAAGCCCAGC | TCCCTGTGAT | 2220 |
| TGAGAATAAA | GTGTGCAATC | GCTATGAGTT | TCTGAATGGA | AGAGTCCAAT | CCACCGAACT | 2280 |
| CTGTGCTGGG | CATTTGGCCG | GAGGCACTGA | CAGTTGCCAG | GGTGACAGTG | GAGGTCCTCT | 2340 |
| GGTTTGCTTC | GAGAAGGACA | AATACATTTT | ACAAGGAGTC | ACTTCTTGGG | GTCTTGGCTG | 2400 |
| TGCACGCCCC | AATAAGCCTG | GTGTCTATGT | TCGTGTTTCA | AGGTTTGTTA | CTTGGATTGA | 2460 |
| GGGAGTGATG | AGAAATAATT | AATTGGACGG | GAGACAG | | | 2497 |

COMPOUND AND METHOD FOR INHIBITING ANGIOGENESIS

TECHNICAL FIELD

The present invention relates to a method of treating pathological states which arise or are exacerbated by angiogenesis. More particularly, the invention relates to a novel compound, compositions and methods of treating angiogenic diseases using a kringle 5 polypeptide of mammalian plasminogen.

BACKGROUND

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e. one of no capillary growth) for prolonged periods which may last for as long as weeks or in some cases, decades. When necessary however (such as during wound repair), these same cells can undergo rapid proliferation and turnover within a 5 day period. (Folkman, J. and Shing, Y., *The Journal of Biological Chemistry*, 267(16): 10931–10934, and Folkman, J. and Klagsbrun, M., *Science*, 235: 442–447 (1987)).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exascerbate an existing pathological condition. For example, ocular neovacularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., *Cancer Research*, 46: 467–473 (1986), Folkman, J., *Journal of the National Cancer Institute*, 82: 4–6 (1989)). It has been shown for example that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as liver, lung or bone (Weidner, N., et al., *The New England Journal of Medicine*, 324(1): 1–8 (1991)).

To date, several naturally occurring angiogenic factors have been described and characterized. (See Fidler, J. I and Ellis, L. M., *Cell*, 79: 185–189 (1994)). Quite recently, O'Reilly, et al. have isolated and purified a 38 kDa protein from serum and urine of tumor-bearing mice that inhibits endothelial cell proliferation (O'Reilly, M. et al., *Cell*, 79: 315–328 (1994) and International Application WO 95/29242, published Nov. 2, 1995, both incorporated herein by reference). Microsequence analysis of this endothelial inhibitor showed it to have 98% identity to an internal fragment of mouse plasminogen. Angiostatin, (as they termed this inhibitory fragment) is a polypeptide which includes the first four kringle regions of mouse plasminogen. A similar fragment from the same region of human plasminogen (i.e. containing kringles 1–4) was also shown to strongly inhibit proliferation of capillary endothelial cells in vitro, while intact plasminogen, was shown not to possess this inhibitory effect. Angiostatin was also shown to be effective in vivo.

Although several angiogenesis inhibitors are currently under development for use in treating angiogenic diseases (Gasparini, G. and Harris, A. L., *J Clin Oncol* 13(3): 765–782, (1995)), there are disadvantages associated with several of these compounds. For example, suramin is a potent angiogenesis inhibitor, but causes (at doses required to reach antitumor activity) severe systemic toxicity in humans. Other compounds, such as retinoids, interferons and antiestrogens are safe for human use but have only a weak anti-angiogenic effect. Still other compounds may be difficult or costly to make. For example, angiostatin may be generated by elastase digestion of lys-plasminogen (discussed below) but preferentially generates a polypeptide containing kringles 1–3. This necessitates the use of large amounts of starting material in order to obtain sufficient quantities of kringle 1–4 polypeptide (i.e. angiostatin).

Thus there is a need for compounds for treating a variety of angiogenic diseases in humans. More specifically, there is a need for angiogenesis inhibitors which are safe for therapeutic use and which exhibit selective toxicity with respect to the pathological condition, such as by selectively inhibiting the proliferation of endothelial cells while exhibiting no or a low degree of toxicity to normal (ie. non-cancerous) human cells. Furthermore, such compounds should be easy and cost-effective to make.

SUMMARY OF THE INVENTION

The present invention provides a compound for the detection and treatment of diseases and processes that are mediated by or associated with angiogenesis. More particularly, the invention provides a compound, referred to as kringle 5, which has a molecular weight of between about 9,000 and 11,000 kilodaltons as determined by reducing polyacrylamide gel electrophoresis and has an amino acid sequence substantially similar to that of a human plasminogen fragment beginning at approximately amino acid position 443 of SEQ ID NO:1. The kringle 5 may be derived from human, mouse, bovine, Rhesus monkey and porcine plasminogen. Preferably, kringle 5 is derived from human plasminogen and has the amino acid sequence of SEQ ID NO:2, SEQ ID NO:3, SEQ ID NO:4, SEQ ID NO:5 and SEQ ID NO:6.

A kringle 5 of the present invention has biological activity in vitro and in vivo. More particularly, a kringle 5 of the present invention is capable of inhibiting angiogenic diseases such as cancer and diabetic retinopathy.

The present invention also includes a method for treating a patient in need of anti-angiogenesis therapy comprising administering to a human or animal a therapeutically effective amount of a mammalian kringle 5 or a biologically active fragment thereof.

The present invention also encompasses a composition comprising an isolated single or double stranded polynucleotide sequence that encodes kringle 5. Such a polynucleotide is preferably a DNA molecule. The invention also includes a vector containing a DNA sequence encoding kringle 5, wherein the vector is capable of expressing kringle 5 when present in a cell, a composition comprising a cell containing a vector, wherein the vector contains a DNA sequence encoding kringle 5 or fragments or analogs thereof, and wherein the vector is capable of expressing kringle 5.

The present invention also includes a composition and a pharmaceutically acceptable excipient.

The present invention also includes a method of making kringle 5 comprising the steps of: (a) exposing a mammalian plasminogen to elastase at a ratio of about 1:100 to about 1:300 to form a mixture of said plasminogen and said elastase; (b) incubating said mixture; and (c) isolating said kringle 5 from said mixture.

BRIEF DESCRIPTION OF THE DRAWINGS

FIGS. 1(a)-1(c) shows the amino acid sequence of human plasminogen (SEQ ID NO:1).

FIGS. 2(a)-2(b) shows the comparative homology in amino acid sequences of human (SEQ ID NO:2), mouse (SEQ ID NO:8), monkey (SEQ ID NO:9), bovine (SEQ ID NO:10), and porcine (SEQ ID NO:11) kringle 5.

FIG. 4(c) shows a summary of $ED_{50}$ values obtained from the inhibition of various kringle fragments on BCE cell proliferation in vitro. In this Figure: kringle 1 represents the sequence of FIG. 1 from amino acid position 80 to amino acid position 163, kringle 2* represents the sequence of FIG. 1 from amino acid position 161 to amino acid position 245, kringle 3* represents the sequence of FIG. 1 from amino acid position 253 to amino acid position 335, kringle 4 represents the sequence of FIG. 1 from amino acid position 354 to amino acid position 443, kringles 2-3* represents the sequence of FIG. 1 from amino acid position 161 to amino acid position 335, kringles 1-3 represent the sequence of FIG. 1 from amino acid position 80 to amino acid position 353, kringles 1-4 represent the sequence of FIG. 1 from amino acid position 80 to amino acid position 443, and kringle 5 represents SEQ ID NO:3. (*=Marti, D., et al., Eur. J. Biochem., 219:455-462 (1994)).

FIGS. 6(a)-6(b) shows the DNA sequence (SEQ ID NO:12) of human plasminogen.

DETAILED DESCRIPTION OF THE INVENTION

Figure 3:
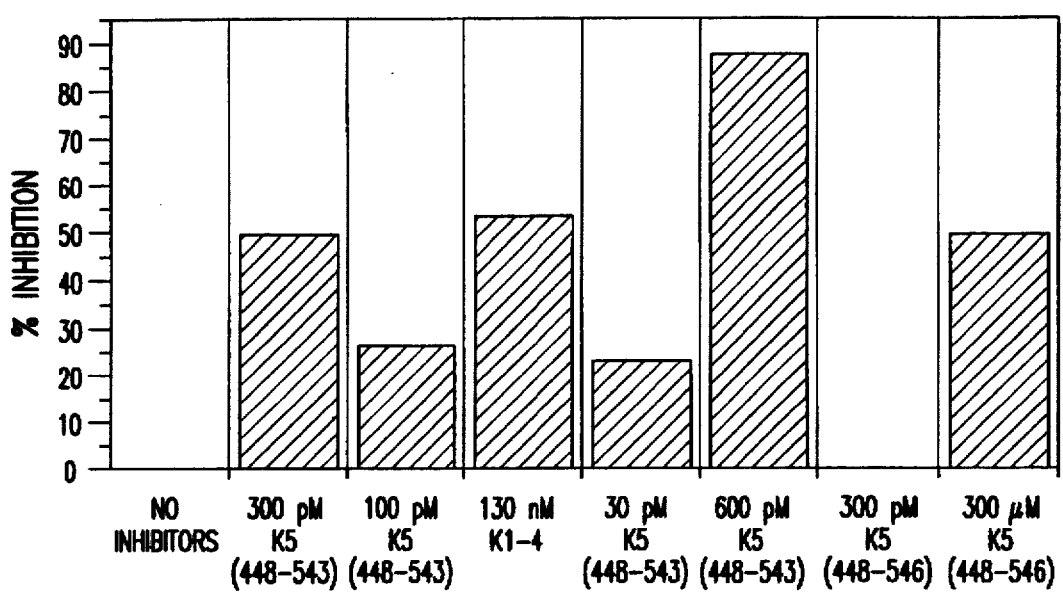
FIG. 3 shows a graph of the anti-proliferative activity of a single dose of various kringle fragments on bovine capillary endothelial (BCE) cells when tested in an in vitro cell proliferation assay.

The present invention provides a compound for the detection and treatment of diseases and processes that are mediated by or associated with angiogenesis. More particularly, the invention provides a compound, referred to as kringle 5, which is effective at inhibiting the process of angiogenesis in vitro and in vivo.

As used here "kringle 5" is a protein defined by three disulfide linkages (described below), and has a molecular weight of between approximately 9,000-11,000 daltons as determined by reducing polyacrylamide gel electrophoresis and has an amino acid sequence substantially similar to that of a human plasminogen fragment beginning at about amino acid position 443 of an intact human plasminogen molecule (see FIG. 1 and SEQ ID NO: 1). The term "substantially similar" when used in reference to kringle 5 amino acid sequences means an amino acid sequence having antiangiogenic activity and having a molecular weight of approximately 9,000 daltons to 11,000 daltons, which also has a high degree of sequence homology to the peptide fragment of human plasminogen beginning approximately at amino acid position 443 in human plasminogen. A "high degree of homology" as used herein means approximately 60% amino acid identity, desirably at least approximately 70% amino acid identity, and more desirably approximately 80% amino acid identity. The terms "angiogenesis inhibiting activity" and "anti-angiogenic activity" refers to the capability of a molecule to inhibit the growth of blood vessels. The term "endothelial inhibiting activity" as used herein means the capability of a molecule to inhibit angiogenesis in general and, for example, to inhibit the growth of bovine capillary endothelial cells in culture in the presence of fibroblast growth factor or other known growth factors.

The amino acid sequence of the complete human plasminogen molecule is shown in FIG. 1 and in SEQ ID NO:1. The sequence of human kringle 5 may begin at any of three different amino acid positions, i.e. at about 443, 449 or 454, depending upon the manner in which the kringle 5 polypeptide is produced. For example, certain forms of kringle 5 may be produced by complete proteolytic cleavage of miniplasminogen using the enzyme elastase. When produced in this manner, the carboxy terminus of the peptide resides at about amino acid 543 of SEQ ID NO.1 but the N-terminal amino acid may begin at any of three different amino acid positions, that is, at about amino acid position 443, 449 or 454. Thus the kringle 5 polypeptide resulting from elastase digestion of miniplasminogen may have a total length of either 101, 95 or 90 amino acids. When produced in this manner, a pool of these three fragments is obtained wherein about 60% of the fragments have a length of 95 amino acids, about 35% of the fragments have the length of 101 and about 5% of the fragments have a length of 90 amino acids. If desired, these various fragments may be further purified by means well known in the art.

Alternatively, kringle 5 may be produced by limited proteolytic cleavage of lys-plasminogen or miniplasminogen using the enzymes elastase and pepsin. Lys-plasminogen refers to a naturally truncated form of plasminogen which circulates in blood and has an amino terminus beginning at about amino acid position 78 of SEQ. ID NO:1 and a carboxyl terminus ending at about amino acid position 790. Miniplasminogen, arises from limited elastase digestion of lys-plasminogen and results in a truncated form of plasminogen having the three amino termini described above (i.e. at about amino acid positions 443, 449, and 454) and a carboxy terminus at about amino acid position 790. Pepsin digestion of either miniplasminogen or lys-plasminogen cleaves these peptides between amino acid positions 547 and 546 of SEQ ID NO:1 resulting in a kringle 5 peptide having Phe (amino acid position 546) as the carboxyl terminal amino acid. Thus, kringle 5 peptides prepared from limited cleavage of lys-plasminogen with elastase and pepsin (or of miniplasminogen with pepsin) may have a total length of either 104, 98 or 93 amino acids. A summary of these kringle 5 peptides is shown in Table 2 below:

TABLE 2

| SEQ ID NO: | Kringle 5 Peptides (ref. FIG. 1) | Total Length |
|---|---|---|
| 2 | From aa position 443 to aa position 543 | 101 |
| 3 | From aa position 449 to aa position 543 | 95 |
| 4 | From aa position 454 to aa position 543 | 90 |
| 5 | From aa position 443 to aa position 546 | 104 |
| 6 | From aa position 449 to aa position 546 | 98 |
| 7 | From aa position 454 to aa position 546 | 93 |

The amino acid sequence of a human kringle 5 having 95 amino acids (specifically SEQ ID NO:2 above) is shown in FIG. 2 in comparison with the sequences of corresponding plasminogen fragments from mouse (SEQ ID NO:8), Rhesus monkey (SEQ ID NO:9), bovine (SEQ ID NO:10) and porcine (SEQ ID NO:11) plasminogen. Given that these sequences are identical in at least 73% of their amino acids, it is to be understood that the amino acid sequence of kringle 5 is substantially similar among species. Thus, the amino acid sequence of the kringle 5 of the present invention may vary depending upon the species from which the plasminogen is derived. Furthermore, although the total number of amino acids in kringle 5 cannot be defined precisely, any particular kringle 5 can be defined on the basis of its molecular weight. (For molecular weights, see Yakovlev, S. A., et al., Thrombosis Research, 79(4): 423–428 (1995) and Niewuwenhuizen, W. and Keyser, J. Thrombosis Research, 38(6): 663–670 (1985), both of which are incorporated herein by reference).

Kringle 5 of the present invention has a specific three dimensional conformation that is defined by the fifth kringle region of the human plasminogen molecule. As shown in SEQ ID. NO:1, kringle 5 comprises 6 cysteine residues capable of forming three disulfide bonds. One such disulfide bond links the cysteine residues located at amino acid positions 462 and 541, a second links the cysteine residues located at amino acid positions 483 and 524 and a third links the cysteine residues located at amino acid positions 512 and 536. Thus, a kringle 5 of the present invention is a polypeptide which comprises a sequence having at least all three of the aforementioned disulfide bonds, however the actual total length of the peptide may vary depending upon the manner in which the kringle 5 fragment is obtained or may vary somewhat in sequence, depending upon the species from which it is obtained.

A kringle 5 polypeptide of the present invention may be further characterized on the basis of potency when tested for its ability to inhibit the growth of BCE cells in vitro. The data in FIG. 3 illustrates that kringle 5 (SEQ ID NO:3) has a 100-fold increase in activity (i.e. at inhibiting bovine capillary endothelial cell proliferation) as compared to kringle 5 (SEQ ID NO:6) and a 400-fold increase in activity as compared to kringle 1–4.

The present invention also contemplates amino acid residue sequences that are substantially duplicative of the sequences set forth herein such that those sequences demonstrate like biological activity to disclosed kringle 5 sequences. Such contemplated sequences include those analogous sequences characterized by a minimal change in amino acid residue sequence or type (e.g., conservatively substituted sequences) which insubstantial change does not alter the fundamental nature and biological activity of the aforementioned sugar biosynthesis enzymes.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

Thus it is to be understood that the present invention is contemplated to encompass any derivatives of kringle 5 that have anti-angiogenic activity and includes the entire class of kringle 5 polypeptides described herein, derivatives of those polypeptides and biologically-active kringle 5 polypeptides. Additionally, the invention is not dependent on the manner of making the kringle 5, i.e. a kringle 5 polypeptide of the present invention includes one which is made (1) by proteolytic cleavage of an isolated mammalian plasminogen (2) by expression of a recombinant molecule having a polynucleotide which encodes an amino acid sequence of kringle 5 and (3) synthetically by means known to those of ordinary skill in the art, as will be described below.

The compounds of the invention, including but not limited to those specified in the examples, possess anti-angiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds or genes which encode their expression may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints'; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, i.e. keloids. Another use is as a birth control agent, by inhibiting ovulation and establishment of the placenta. Kringle 5 is also useful in the treatment of diseases that have angiogenesis as a pathologic consequence such as cat scratch disease (*Rochele minalia quintosa*) and ulcers (*Helicobacter pylori*).

Kringle 5 may be used in combination with other compositions and procedures for the treatment of diseases. For example, a tumor may be treated conventionally with surgery, radiation or chemotherapy combined with kringle 5 and then kringle 5 may be subsequently administered to the patient to extend the dormancy of micrometastases and to stabilize and inhibit the growth of any residual primary tumor. Additionally, kringle 5, kringle 5 fragments, kringle 5 antisera, kringle 5 receptor agonists, kringle 5 receptor antagonists, or combinations thereof, may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Cytotoxic agents such as ricin, may be linked to kringle 5, and high affinity kringle 5 peptide fragments, thereby providing a tool for destruction of cells that bind kringle 5. Peptides linked to cytotoxic agents may be infused in a manner designed to maximize delivery to the desired location. For example, ricin-linked high affinity kringle 5 fragments may be delivered through a cannula into vessels supplying the target site or directly into the target. Such agents may also be delivered in a controlled manner through osmotic pumps coupled to infusion cannulae. A combination of kringle 5 antagonists may be co-applied with stimulators of angiogenesis to increase vascularization of tissue. Therapeutic regimens of this type could provide an effective means of destroying metastatic cancer.

The present invention also encompasses gene therapy whereby the gene encoding kringle 5 is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335-356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene which encodes a protein product that will treat the condition or that will make the tissue or organ more susceptible to a treatment regimen. As an example of a prophylactic strategy, a gene encoding kringle 5 may be placed in a patient and thus prevent occurrence of angiogenesis; or a gene that makes tumor cells more susceptible to radiation could be inserted so that radiation of the tumor would cause increased killing of the tumor cells.

Many protocols for transfer of kringle 5 DNA or kringle 5 regulatory sequences are envisioned in this invention. Transfection of promoter sequences, other than one specifically associated with kringle 5, or other sequences which would increase production of kringle 5 protein are also envisioned as methods of gene therapy. An example of this technology is found in Transkaryotic Therapies, Inc., of Cambridge, Mass., using homologous recombination to insert a "genetic switch" that turns on an erythropoietin gene in cells. See Genetic Engineering News, Apr. 15, 1994. Such "genetic switches" could be used to activate kringle 5 (or a kringle 5 receptor) in cells not normally expressing these proteins.

Gene transfer methods for gene therapy fall into three broad categories: (1) physical (e.g., electroporation, direct gene transfer and particle bombardment), (2) chemical (e.g. lipid-based carriers and other non-viral vectors) and (3) biological (e.g. virus derived vectors). For example, non-viral vectors such as liposomes coated with DNA may be directly injected intravenously into the patient. It is believed that the liposome/DNA complexes are concentrated in the liver where they deliver the DNA to macrophages and Kupffer cells. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses. In vivo gene transfer involves introducing the DNA into the cells of the patient when the cells are within the patient. All three of the broad based categories described above may be used to achieve gene transfer in vivo, ex vivo, and in vitro.

Mechanical (i.e. physical) methods of DNA delivery can be achieved by direct injection of DNA, such as microinjection of DNA into germ or somatic cells, pneumatically delivered DNA-coated particles, such as the gold particles used in a "gene gun," and inorganic chemical approaches such as calcium phosphate transfection. It has been found that physical injection of plasmid DNA into muscle cells yields a high percentage of cells which are transfected and have a sustained expression of marker genes. The plasmid DNA may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer may also be employed for injecting DNA into cells, tissues and organs. With a particle bombardment device, or "gene gun," a motive force is generated to accelerate DNA-coated high density particles (such as gold or tungsten) to a high velocity that allows penetration of the target organs, tissues or cells. Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. The techniques of particle-mediated gene transfer and electroporation are well known to those of ordinary skill in the art.

Chemical methods of gene therapy involve carrier mediated gene transfer through the use of fusogenic lipid vesicles such as liposomes or other vesicles for membrane fusion. A carrier harboring a DNA of interest, can be conveniently introduced into body fluids or the bloodstream and then site specifically directed to the target organ or tissue in the body. Liposomes for example, can be developed which are cell specific or organ specific and thus the foreign DNA carried by the liposome will be taken up by those specific cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer.

Transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Carrier mediated gene transfer may also involve the use of lipid-based compounds which are not liposomes. For example, lipofectins and cytofectins are lipid-based positive ions that bind to negatively charged DNA, forming a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream; target cells that have the cell surface receptor will specifically bind the ligand and transport the ligand-DNA complex into the cell.

Biological gene therapy methodologies employ viral vectors to insert genes into cells. The term "vector" as used herein means a carrier that can contain or associate with specific polynucleotide sequences and which functions to transport the specific polynucleotide sequences into a cell. The transfected cells may be cells derived from the patient's normal tissue, the patient's diseased tissue, or may be non-patient cells. Examples of vectors include plasmids and infective microorganisms such as viruses, or non-viral vectors such as the ligand-DNA conjugates, liposomes, and lipid-DNA complexes discussed above.

It may be desirable that a recombinant DNA molecule comprising a kringle 5 DNA sequence is operatively linked to an expression control sequence to form an expression vector capable of expressing kringle 5. Alternatively, gene regulation of kringle 5 may be accomplished by administering compounds that bind to the kringle gene, or control regions associated with the kringle 5 gene, or its corresponding RNA transcript to modify the rate of transcription or translation.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome. For example, altered retrovirus vectors have been used in ex vivo methods to introduce genes into peripheral and tumor-infiltrating lymphocytes, hepatocytes, epidermal cells, myocytes, or other somatic cells (which may then introduced into the patient to provide the gene product from the inserted DNA).

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

When used in the above or other treatments, a therapeutically effective amount of one of the compounds of the present invention may be employed in pure form or, where such forms exist, in pharmaceutically acceptable salt form. By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as maleic acid, succinic acid and citric acid. Other salts include salts with alkali metals or alkaline earth metals, such as sodium, potassium, calcium or magnesium or with organic basis. Preferred salts of the compounds of the invention include phosphate, tris and acetate.

The total daily dose of the compounds of this invention administered to a human or lower animal may range from about 0.001 to about 1 mg/kg of patients body mass/day. If desired, the effective daily dose may be divided into multiple doses for purposes of administration; consequently, single dose compositions may contain such amounts or submultiples thereof to make up the daily dose.

Alternatively, a compound of the present invention may be administered as pharmaceutical compositions containing the compound of interest in combination with one or more pharmaceuticlly acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters) and poly (anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically-acceptable ophthalmic vehicle may, for example, be an ointment, vegetable oil or an encapsulating material. Alternatively, the a compound of the invention may be injected directly into the vitrious and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, when used in the treatment of solid tumors, compounds of the invention may be administered with anti-neoplastic agents such as alpha interferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like.

Total daily dose of kringle 5 (administered in combination with a compound of this invention) to be administered to a human or other mammal host in single or divided doses may be in amounts, for example, from 0.0001 to 300 mg/kg body weight daily and more usually 1 to 300 mg/kg body weight.

It will be understood that agents which can be combined with the compound of the present invention for the inhibition, treatment or prophylaxis of angiogenic diseases are not limited to those listed above, but include in principle any agents useful for the treatment or prophylaxis of angiogenic diseases.

Synthetic peptide fragments of kringle 5 may also be produced and used in a variety of applications. As examples, different peptide fragments of kringle 5 can be used (1) as agonists and antagonists active at kringle 5 binding sites, (2) as a means to isolate a kringle 5 receptor, (3) as antigens for the development of specific antisera, (4) as peptides for use in diagnostic kits and (5) as peptides linked to or used in combination with cytotoxic agents (for targeted killing of cells that bind kringle 5. The amino acid sequences that comprise these peptides may be selected on the basis of their position on the exterior regions of the molecule which are accessible for binding to antisera. Furthermore, these peptide sequences may be compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules, thereby enhancing the potential for high specificity in the development of antisera, agonists and antagonists to kringle 5.

Systematic substitution of amino acids within these synthesized peptides may yield high affinity peptide agonists and antagonists to the kringle 5 receptor that enhance or diminish kringle 5 binding to its receptor. Such agonists may be used to suppress the growth of micrometastases, thereby limiting the spread of cancer. In cases of inadequate vascularization, antagonists to kringle 5 may be applied to block the inhibitory effects of kringle 5 and promote angiogenesis. For example, this type of treatment may have therapeutic effects in promoting wound healing in diabetics.

Kringle 5 peptides may also be employed to develop affinity columns for isolation of a kringle 5 receptor in for example, cultured endothelial cells. As is known in the art, isolation and purification of a kringle 5 receptor may be followed by amino acid sequencing to identify and isolate polynucleotides which encode the kringle 5 receptor. Such polynucleotides may then be cloned into a suitable expression vector and transfected into tumor cells. Expression of the receptor by the transfected tumor cells would enhance the responsiveness of these cells to endogenous or exogenous kringle 5, thereby decreasing the rate of metastatic growth. Furthermore, recombinant expression of this receptor would allow greater amounts of receptor to be produced, e.g. to produce a sufficient quantity for use in high throughput screening assays to identify smaller antagonists which mimic the action of kringle 5.

Kringle 5 peptides of the present invention can also be used as antigens to generate polyclonal or monoclonal antibodies that are specific for the kringle 5 inhibitor. One way in which such antibodies could be used is in diagnostic methods and kits to detect or quantify kringle 5 in a body fluid or tissue. Results from these tests could be used to diagnose or determine the prognostic relevance of kringle 5.

Kringle 5 peptides may be chemically coupled to isotopes, enzymes, carrier proteins, cytotoxic agents, fluorescent molecules, chemiluminescent, bioluminescent and other compounds for a variety of applications. For example, a kringle 5 polypeptide may be labeled to facilitate testing of its ability to bind kringle 5 antisera or to detect cell types which possess a kringle 5 receptor. The coupling technique is generally chosen on the basis of the functional groups available on the amino acids of the kringle 5 sequence including, but not limited to amino, sulfhydral, carboxyl, amide, phenol, and imidazole. Various reagents used to effect such couplings include among others, glutaraldehyde, diazodzed benzidine, carbodiimide, and p-benzoquinone.

The efficiency of the coupling reaction is determined using different techniques appropriate for the specific reaction. For example, radiolabeling of a kringle 5 peptide with $I^{125}$ may be accomplished using chloramine T and $NaI^{125}$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, a labeled kringle 5 peptide may be obtained which is free from unreacted $NaI^{125}$.

Another application of peptide conjugation is for production of polyclonal antisera. For example, kringle 5 peptides containing lysine residues may be linked to purified bovine serum albumin using glutaraldehyde. The efficiency of this reaction may be determined by measuring the incorporation of radiolabeled peptide. Unreacted glutaraldehyde and peptide may be separated by dialysis and the conjugate stored for subsequent use.

The production of antiserum against kringle 5, kringle 5 analogs, peptide fragments of kringle 5 and the kringle 5 receptor can be performed using established techniques known to those skilled in the art. For example, polyclonal antisera may be raised in rabbits, sheep, goats or other animals. Kringle 5 peptides conjugated to a carrier molecule such as bovine serum albumin, or kringle 5 itself, may be combined with an adjuvant mixture, emulsified and injected subcutaneously at multiple sites on the back, neck, flanks, and sometimes in the footpads of a suitable host. Generally, booster injections are then given at regular intervals, such as every 2 to 4 weeks. Approximately 7 to 10 days after each injection, blood samples are obtained by venipuncture, using, for example, the marginal ear veins after dilation. The blood samples are allowed to clot overnight at 4° C. and are centrifuged at approximately 2400 X g at 4° C. for about 30 minutes. The serum is removed, aliquoted, and stored at 4° C. for immediate use or at −20° to −90° C. for subsequent analysis.

Serum samples from generation of polyclonal antisera or media samples from production of monoclonal antisera may be analyzed for determination of antibody titer and in particular, for the determination of high titer antisera. Subsequently, the highest titer kringle 5 antisera may be tested to establish the following; a) optimal antiserum dilution for highest specific binding of the antigen and lowest non-specific binding, b) ability to bind increasing amounts of kringle 5 peptide in a standard displacement curve, c) potential cross-reactivity with related peptides and proteins, including plasminogen and also kringle 5 of related species, and d) ability to detect kringle 5 peptides in extracts of plasma, urine, tissues, and in cell culture media.

Titer may be established through several means known in the art, such as by dot blot and density analysis, and also by precipitation of radiolabeled peptide-antibody complexes using protein A, secondary antisera, cold ethanol or charcoal-dextran followed by activity measurement with a gamma counter. If desired, the highest titer antisera may be purified on affinity columns. For example, kringle 5 peptides may be coupled to a commercially available resin and used to form an affinity column. Antiserum samples may then be passed through the column so that kringle 5 antibodies bind (via kringle 5) to the column. These bound antibodies are subsequently eluted, collected and evaluated for determination of titer and specificity.

Kits for measurement of kringle 5, and the kringle 5 receptor, are also contemplated as part of the present invention. Antisera that possess the highest titer and specificity and can detect kringle 5 peptides in extracts of plasma, urine, tissues, and in cell culture media may be used to establish assay kits for rapid, reliable, sensitive, and specific measurement and localization of kringle 5. These assay kits may employ (but are not limited to) the following techniques: competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established by means well known to those skilled in the art.

One example of an assay kit commonly used in research and in the clinic is a radioimmunoassay (RIA) kit. A kringle 5 RIA may be established in the following manner: After successful radioiodination and purification of kringle 5 or a kringle 5 peptide, antiserum possessing the highest titer of anti-kringle 5 antibodies is added at several dilutions to tubes containing a relatively constant amount of radioactivity, such as 10,000 cpm, in a suitable buffer system. (Buffer or preimmune serum is added to other tubes to determine non-specific binding). After incubation at 4° C. for 24 hours, protein A is added to all tubes and the tubes are vortexed, incubated at room temperature for 90 minutes, and centrifuged at approximately 2000–2500 X g at 4° C. to precipitate the complexes of antibody bound to labeled antigen. The supernatant is removed by aspiration and radioactivity in the pellets counted in a gamma counter. The antiserum dilution that binds approximately 10 to 40% of the labeled peptide after subtraction of the non-specific binding is selected for further characterization.

Next, a dilution range (approximately 0.1 pg to 10 ng) of the kringle 5 peptide used for development of the antiserum is evaluated by adding known amounts of the peptide to tubes containing radiolabeled peptide and antiserum. After an incubation period, for example, 24 or 48 hours, protein A is added and the tubes centrifuged, the supernatant removed and the radioactivity in the pellet counted. The displacement of the binding of radiolabeled kringle 5 peptide by the unlabeled kringle 5 peptide (standard) provides a standard curve. In addition, several concentrations of other kringle 5 peptide fragments, plasminogen, kringle 5 from different species, and homologous peptides may be added to the assay tubes to characterize the specificity of the kringle 5 antiserum.

Thereafter, extracts of various tissues, including but not limited to primary and secondary tumors, Lewis lung carcinoma, cultures of kringle 5 producing cells, placenta, uterus, and other tissues such as brain, liver, and intestine, are prepared using extraction techniques that have been successfully employed to extract kringle 5. After lyophilization or Speed Vac of the tissue extracts, assay buffer is added and different aliquots are placed into the RIA tubes. Extracts of known kringle 5 producing cells produce displacement curves that are parallel to the standard curve, whereas extracts of tissues that do not produce kringle 5 do not displace radiolabeled kringle 5 from the kringle 5 antiserum. Such displacement curves indicate the utility of the kringle 5 assay to measure kringle 5 in tissues and body fluids.

Tissue extracts that contain kringle 5 may also be characterized by subjecting aliquots to reverse phase HPLC. Eluate fractions are collected, dried in Speed Vac, reconstituted in RIA buffer and analyzed in the kringle 5 RIA. In this case, the maximal amount of kringle 5 immunoreactivity is located in the fractions corresponding to the elution position of kringle 5.

The above described assay kit would provide instructions, antiserum, kringle 5 or kringle 5 peptide, and possibly radiolabeled kringle 5 and/or reagents for precipitation of bound kringle 5/kringle 5 antibody complexes. Such a kit would be useful for the measurement of kringle 5 in biological fluids and tissue extracts of animals and humans with and without tumors.

Another kit may be used to visualize or localize kringle 5 in tissues and cells. For example, immunohistochemistry techniques and kits which employ such techniques are well known to those of ordinary skill in the art. As is known in the art, an immunohistochemistry kit would provide kringle 5 antiserum, and possibly blocking serum and secondary antiserum linked to a fluorescent molecule such as fluorescein isothiocyanate, or to some other reagent used to visualize the primary antiserum. Using this methodology, biopsied tumors may be examined for sites of kringle 5 production or for sites of the kringle 5 receptor. Alternatively, a kit may supply radiolabeled nucleic acids for use in in situ hybridization to probe for kringle 5 messenger RNA.

The compounds of the invention may be prepared using processes well known to those of ordinary skill in the art. (See for example, Sottrup-Jensen et al., Progress in Chemical Fibrinolysis and Thrombolysis, Vol. 3, Davidson, J. F., Rowan, R. M., Samama, M. M. and Desnoyers, P. C. editors, Raven Press, New York, 1978). One manner of preparing kringle 5 polypeptides is by enzymatic cleavage of the native protein (glu-plasminogen) or a variant thereof (meaning a truncated form of the full length protein which is amenable to cleavage by enzymatic digestion and which comprises at least a kringle 5 sequence as defined above). This method first requires isolating the protein from human plasma in the absence of plasmin inhibitors, thereby promoting the conversion of glu-plasminogen to lys-plasminogen (see Novokhatny, V and Kudinov, S. A., J. Mol. Biol. 179: 215–232 (1984)). Subsequently, the truncated molecule is treated with an proteolytic enzyme at a concentration sufficient to cleave kringle 5 from the polypeptide and then purified from the remaining fragments by means known in the art. A preferred proteolytic enzyme is elastase which cleaves plasminogen and its truncated variants between kringle regions 3–4 and 4–5 (and is thereby capable of forming polypeptides containing kringles 1–3 and 1–4 or kringles 4 or 5 alone). As an example, lys-plasminogen may be treated with porcine or human neutrophyl elastase at a ratio of about 1:100–1:300 lys-plasminogen:elastase but preferably at a ratio of 1:150–1:250 and most preferably at a ratio of 1:150 in a buffer solution (such as Tris-HCl, NaCl, sodium phosphate and the like). (Alternatively, the elastase may first be immobilized (such as to a resin) to facilitate purification of the cleavage products). The lys-plasminogen is generally treated with porcine elastase at a temperature ranging from about 10° C. to about 40° C. and for time periods ranging from about 4 to about 24 hours depending on the extent of cleavage desired. To achieve complete digestion of lys-plasminogen or miniplasminogen with elastase requires exposure of these polypeptides to the enzyme for at least about 12 hours at room temperature. Varying the pH and exposure time to the enzyme results in less or partial cleavage at one or more of the susceptible cleavage sites. The cleavage products are then purified by any means well known in the art (such as by column chromatography). A preferred purification scheme involves applying the cleavage products to a lysine-Sepharose column as described in Example 1 below.

Figure 5:
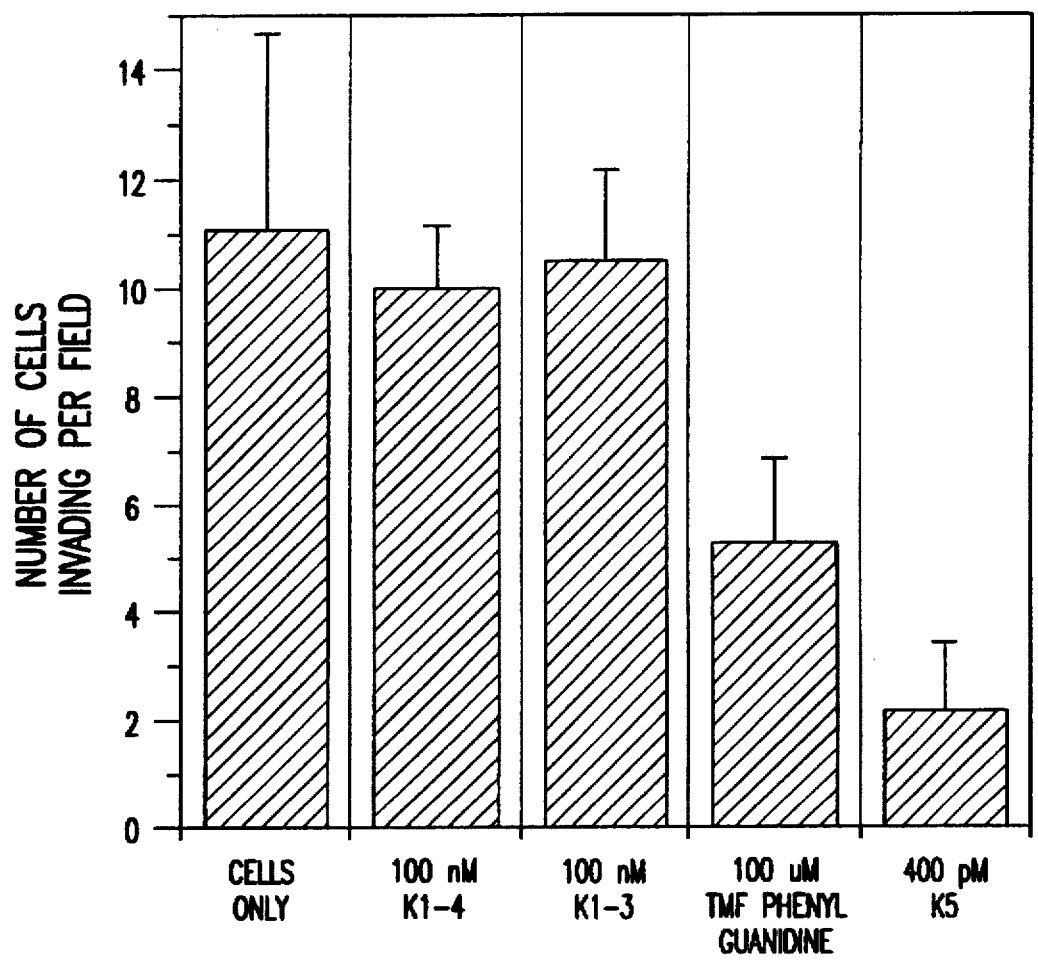
FIG. 5 shows a graph of the effect of various kringle fragments on inhibition of endothelial cell migration in vitro.

Alternatively, a kringle 5 polypeptide or biologically active fragments thereof, may be obtained by expression of a recombinant molecule comprising a polynucleotide having a sequence which encodes kringle 5 (and preferably kringle 5 having a carboxyl terminus at amino acid position 543) and then purifying the polypeptide product which is expressed (see Menhart, N., et al, Biochemistry, 32: 8799–8806 (1993) incorporated herein by reference). The DNA sequence of human plasminogen has been published (Browne, M. J. et al. Fibrinolysis, 5(4): 257–260 (1991), incorporated herein by reference) and is shown in FIG. 5 (SEQ ID NO:12). A polynucleotide sequence encoding kringle 5 (SEQ ID NO:3) begins at about nucleotide position 1421 of SEQ ID NO:12 and ends at about nucleotide position 1723. This method of making a kringle 5 polypeptide employs conventional techniques of molecular biology, microbiology, recombinant DNA, and immunology, all of which are within the skill of the art and are fully explained in the literature. (See for example, "Molecular Cloning: A Laboratory Manual" Second Edition by Sambrook et al., Cold Spring Harbor Press, 1989). For example, the gene for kringle 5 may be isolated from cells or tissues that express high levels of kringle 5 by (1) isolating messenger RNA from the tissue or cells, (2) using reverse transcriptase to generate the corresponding DNA sequence and then (3) using the polymerase chain reaction (PCR) with the appropriate primers to amplify the DNA sequence coding for the active kringle 5 amino acid sequence. Furthermore, a polynucleotide encoding a kringle 5 polypeptide may be cloned into any commercially available expression vector (such as pBR322, pUC vectors and the like) or expression/purification vectors (such as a GST fusion vector, Pharmacia, Piscataway, N.J.) and then expressed in a suitable procaryotic, viral or eucaryotic host. Purification may then be achieved by conventional means or in the case of a commercial expression/purification system, in accordance with manufacturer's instructions.

Polypeptides of kringle 5, or biologically active fragments thereof, may be synthesized by standard methods of solution or solid phase chemistry known to those of ordinary skill in the art. For example kringle 5 may be synthesized by solid phase chemistry techniques following the procedures described by Steward and Young (Steward, J. M. and Young, J. D., Solid Phase Peptide Synthesis, 2nd Ed., Pierce Chemical Company, Rockford, Ill., (1984)), using an Applied Biosystem synthesizer. Similarly, multiple fragments can be synthesized which are subsequently linked together to form larger fragments. These synthetic peptide fragments can also be made with amino acid substitutions at specific locations to test for kringle 5-like activity in vitro and in vivo.

The invention will be better understood in connection with the following examples, which are intended as an illustration of and not a limitation upon the scope of the invention. That is, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

General Methodologies

1. Isolation and Purification of Kringle 5: Kringle 5 fragment was prepared from the digestion of Lys-HPg (Abbott Laboratories, Abbott Park, Ill.) with porcine elastase (SIGMA, St. Louis, Mo.) by a modification of the method of Powell et al. in Arch Biochem. Biophys. 248(1): 390–400 (1986). Briefly, 1.5 mg of porcine elastase was incubated with 200 mg of Lys-HPg in 50 mM Tris-HCl pH 8.0 and rocked overnight at room temperature. The reaction was terminated by the addition of diisopropyl fluorophosphate (DFP, obtained from SIGMA) to a final concentration of 1 mM. The mixture was rocked for an additional 30 minutes then dialysed against 50 mM Tris pH 8.0 overnight and concentrated. The cleaved HPg was placed over a lysine-Sepharose 4B column (2.5 cm×15 cm) (Brockway, W. J. and Castellino, F. J., Arch. Biochem. Biophys. 151: 194–199 (1972)) equilibrated with 50 mM Tris pH 8.0 until an absorbance of 0.05 (at 280 nm) was reached. (This step was performed to effect removal of any fragments containing a kringle 1 region and/or a kringle 4 region (both of which bind lysine). The non-absorbed kringle fragments were then dialysed against 50 mM $Na_2PO_4$ buffer, pH 5.0. After dialysis of the kringle fraction the material was applied to a BioRad Mono-S column equilibrated with the same buffer. The cleaved kringle 5 portion, uncut mini-HPg and the remaining protease domain fraction were eluted with a 0–20%,20–50% and 50–70% step gradient of 20 mM Phosphate/1M KCl pH 5.0. The kringle 5 fragment was eluted at the 50% step as determined by gel electrophoresis. The collected peak was dialysed overnight against 20 mM Tris pH 8.0.

The separated kringle 5 fragment was determined to be at least 95% pure by FPLC chromatography and DodSO4/PAGE with silver staining (Coomasie Blue). Sequence analysis of the amino terminal portion of the purified fragments revealed the presence of three polypeptides having N-terminal sequences of VLLPDVETPS, VAPPPVVLL and VETPSEED which correspond to amino acid positions 449–458, 443–450 and 454–461 of SEQ ID. NO:1 respectively.

2. Endothelial Proliferation Assay: The in vitro proliferation of endothelial cells was determined essentially as described by Lingen, et al., in Laboratory Investigation 74: 476–483 (1996), using the Cell Titer 96 Aqueous Non-Radioactive Cell Proliferation Assay kit (Promega Corporation, Madison, Wis.). Briefly, bovine capillary (adrenal) endothelial cells were plated at a density of 1000 cells per well in a 96-well plate in DMEM containing 10% donor calf serum and 1% BSA (GIBCO BRL, Gaithersburg, Md.). After 8 hours, the cells were starved overnight in DMEM containing 0.1% BSA, then re-fed with media containing specified concentrations of inhibitor and 5 ng/mL bFGF. The results of the assay were corrected both for unstimulated cells (i.e. no bFGF added) as the baseline and for cells stimulated with bFGF alone (i.e. no inhibitor added) as the maximal proliferation. When multple experiments were combined, the results were represented as the percent change in cell number as compared to bFGF alone.

3. Endothelial Cell Migration Assay: The endothelial cell migration assay was performed essentially as described by Polverini, P. J. et al., Methods Enzymol, 198: 440–450 (1991). Briefly, bovine capillary (adrenal) endothelial cells (BCE, supplied by Judah Folkman, Harvard University Medical School) were starved overnight in DMEM containing 0.1% bovine serum albumin (BSA). Cells were then harvested with trypsin and resuspended in DMEM with 0.1% BSA at a concentration of $1.5 \times 10^6$ cells/mL. Cells were added to the bottom of a 48-well modified Boyden chamber (Nucleopore Corporation, Cabin John, Md.). The chamber was assembled and inverted, and cells were allowed to attach for 2 hours at 37° C. to polycarbonate chemotaxis membranes (5 μm pore size) that had been soaked in 0.1% gelatin overnight and dried. The chamber was then reinverted and test substances were added to the wells of the upper chamber (to a total volume of 50 μL); the apparatus was then incubated for 4 hours at 37° C. Membranes were recovered, fixed and stained (DiffQuick, Fisher Scientific, Pittsburgh, Pa.) and the number of cells that had migrated to the upper chamber per 10 high power fields were counted. Background migration to DMEM+0.1% BSA was subtracted and the data reported as the number of cells migrated per 10 high power fields (400X) or when results from multiple experiments were combined, as the percent inhibition of migration compared to a positive control.

EXAMPLE 2

Effect of Kringle 5 on Endothelial Cell Proliferation in vitro

Figure 4A:
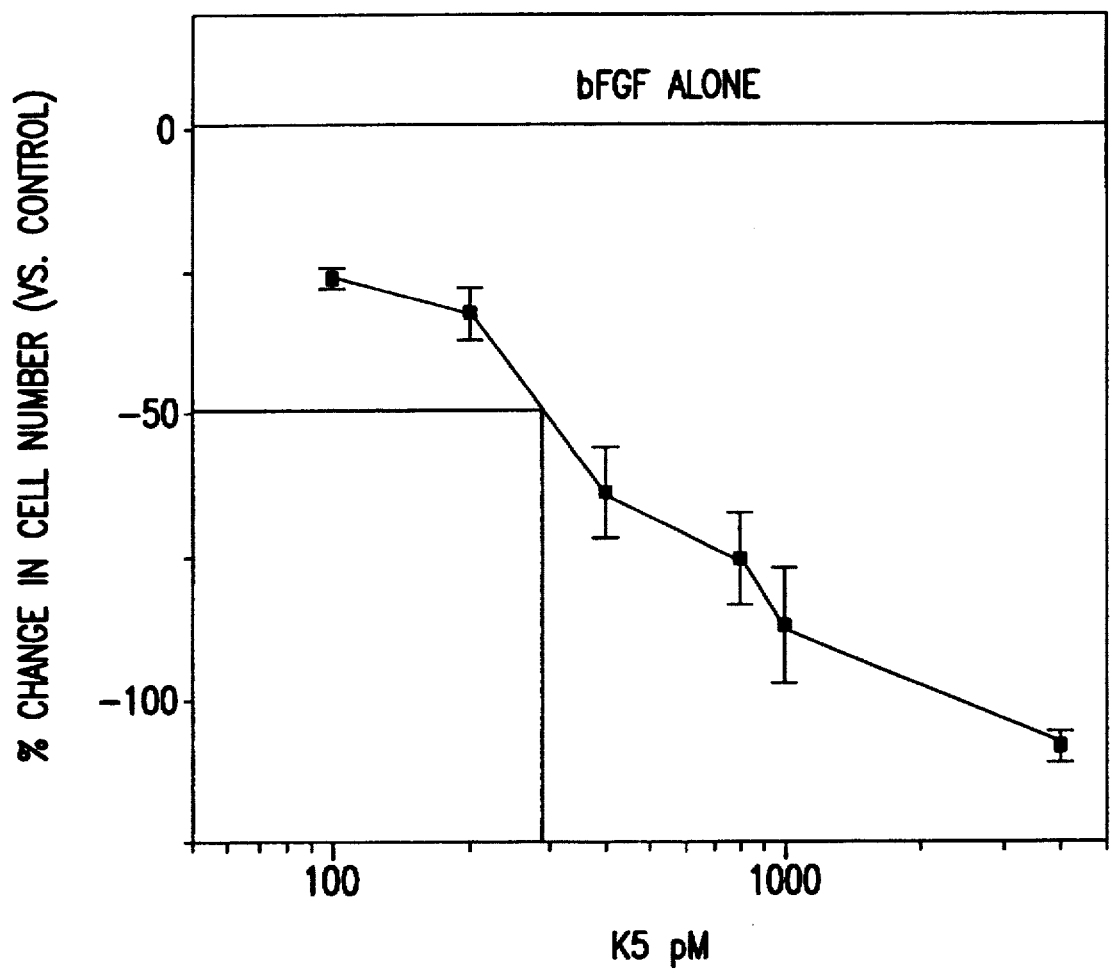
FIG. 4(a) shows a graph of the anti-proliferative activity of various concentrations of kringle 5 (SEQ ID NO:3) on (BCE) cells when tested in an in vitro cell proliferation assay.
Figure 4B:
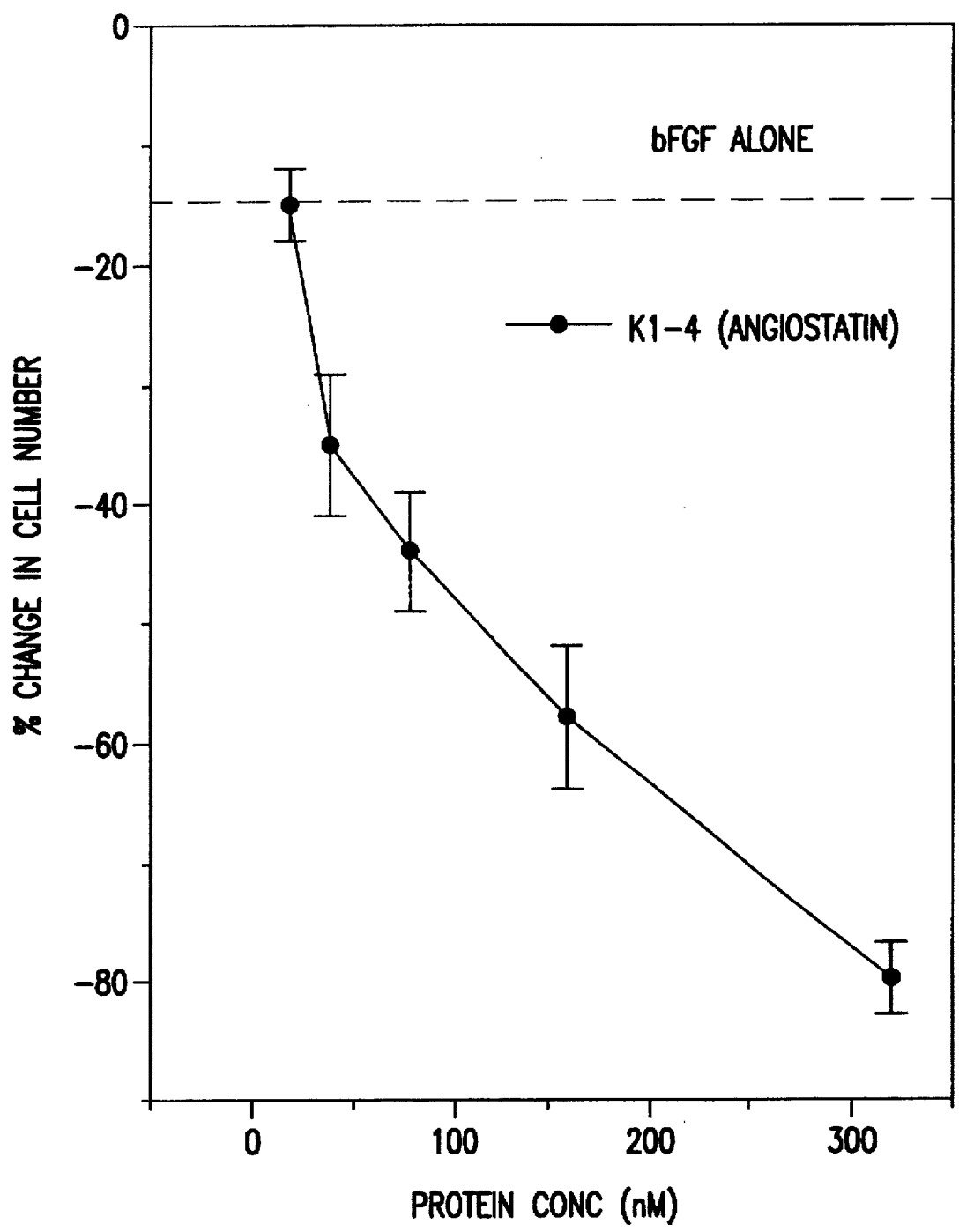
FIG. 4(b) shows a graph of the anti-proliferative activity of various concentrations of kringles 1-4 on BCE cells when tested in an in vitro cell proliferation assay.

The effect of kringle 5 on endothelial cell proliferation was determined in vitro using the above described endothelial cell proliferation assay. For these experiments, kringle 5 was prepared as above and tested at various concentrations ranging from about 100 to 1000 pM. bFGF was used as a maximum proliferation control. As FIG. 4(a) shows, kringle 5 (SEQ ID NO:3) was effective at inhibiting BCE cell proliferation in a dose-dependent manner. The concentration of kringle 5 required to reach 50% inhibition ($ED_{50}$) was determined at about 300 pM. ($ED_{50}$ is an absolute measure of potency and is expressed as the negative log of the dose required to elicit of the maximum response). In contrast, the $ED_{50}$ of kringles 1–4 is shown to be 135 nM (see FIG. 4(b)).

A summary of the effect of various kringle fragments on inhibition of BCE cell proliferation is shown in FIG. 4(c). As shown, kringle 3 was least effective at inhibiting BCE cell proliferation ($ED_{50}$=460 nM), followed by kringle 1 ($ED_{50}$=320 nM), kringles 1–4 ($ED_{50}$=135 nM) and kringles 1–3 ($ED_{50}$=75 nM). Kringle 5 was most effective at inhibiting BCE cell proliferation having an $ED_{50}$ of 0.3 nM.

EXAMPLE 3

Effect of Kringle 5 on Endothelial Cell Migration in vitro

The effect of kringle 5 on endothelial cell migration was also determined in vitro using the above described endothelial cell migration assay. As shown in FIG. 5, kringle 5 inhibited BCE cell migration in a dose-dependent fashion with an $ED_{50}$ of approximately 300 pM. At the concentration of kringle 5 required for maximal inhibition of BCE cells, PC-3 cells and MDA 486 cells were also inhibited. This result, taken together with the result in Example 2, indicates that the inhibition of stimulated proliferation and migration of BCE cells by kringle 5 is both potent and specific to endothelial cells, and not to normal or tumor cells.

We claim:

1. An isolated kringle 5 of mammalian plasminogen selected from the group consisting of SEQ ID NO:2, SEQ ID NO:3, SEQ ID NO:4, SEQ ID NO:5, SEQ ID NO:6 and SEQ ID NO:7.
2. The kringle 5 of claim 1 having SEQ ID NO:2.
3. The kringle 5 of claim 1 having SEQ ID NO:3.
4. The kringle 5 of claim 1 having SEQ ID NO:4.
5. The kringle 5 of claim 1 having SEQ ID NO:5.
6. The kringle 5 of claim 1 having SEQ ID NO:6.
7. The kringle 5 of claim 1 having SEQ ID NO:7.
8. A method of treating a patient in need of anti-angiogenesis therapy comprising administering to a human or animal a therapeutically effective amount of a kringle 5 of mammalian plasminogen wherein said kringle 5 has a sequence selected from the group consisting of
   (a) amino acids from about amino acid position 443 to about amino acid position 543 of SEQ ID NO:1;

(b) amino acids from about amino acid position 449 to about amino acid position 543 of SEQ ID NO:1;

(c) amino acids from about amino acid position 454 to about amino acid position 543 of SEQ ID NO:1;

(d) amino acids from about amino acid position 443 to about amino acid position 546 of SEQ ID NO:1;

(e) amino acids from about amino acid position 449 to about amino acid position 546 of SEQ ID NO:1;

(f) amino acids from about amino acid position 454 to about amino acid position 546 of SEQ ID NO:1.

9. The method of claim 8 wherein said kringle 5 has the sequence from about amino acid position 443 to about amino acid position 543 of SEQ ID NO:1.

10. The method of claim 8 wherein said kringle 5 has the sequence from about amino acid position 449 to about amino acid position 543 of SEQ ID NO:1.

11. The method of claim 8 wherein said kringle 5 has the sequence from about amino acid position 454 to about amino acid position 543 of SEQ ID NO:1.

12. The method of claim 8 wherein said kringle 5 has the sequence from about amino acid position 443 to about amino acid position 546 of SEQ ID NO:1.

13. The method of claim 8 wherein said kringle 5 has the sequence from about amino acid position 449 to about amino acid position 546 of SEQ ID NO:1.

14. The method of claim 8 wherein said kringle 5 has the sequence from about amino acid position 454 to about amino acid position 546 of SEQ ID NO:1.

* * * * *